United States Patent
Buehler et al.

(10) Patent No.: US 6,273,152 B1
(45) Date of Patent: Aug. 14, 2001

(54) EXACT DOSE DISPENSER DEVICE ASSEMBLY

(75) Inventors: John D. Buehler; Eric S. Mathias, both of Bridgeton, NJ (US)

(73) Assignee: Comar Inc., Buena, NJ (US)

( * ) Notice: Subject to any disclaimer, the term of this patent is extended or adjusted under 35 U.S.C. 154(b) by 0 days.

(21) Appl. No.: 09/408,832

(22) Filed: Sep. 29, 1999

Related U.S. Application Data

(60) Provisional application No. 60/102,436, filed on Sep. 30, 1998.

(51) Int. Cl.⁷ ........................................................ B65B 1/04
(52) U.S. Cl. ................................. 141/22; 141/94; 222/47; 222/309
(58) Field of Search .................................. 141/22–27, 94; 222/41, 43, 47–50, 309

(56) References Cited

U.S. PATENT DOCUMENTS 5,746,349 * 5/1998 Putterman et al. ..................... 222/49
5,836,359 * 11/1998 Seidler ..................................... 222/23
6,045,003 * 4/2000 Seidler ..................................... 222/48

* cited by examiner

Primary Examiner—Steven O. Douglas
(74) Attorney, Agent, or Firm—Eugene E. Renz, Jr., PC

(57) ABSTRACT

A dosage dispenser assembly for containers to dispense liquids in the containers. The assembly includes elongated hollow barrel and an arrangement for removably mounting the barrel over the discharge opening in the container so that the port in the barrel in the seated position is disposed adjacent the bottom of the container. A stop sleeve of generally tubular configuration engages internally of the barrel and has at least two key ways of different axial depth defining cam follower surfaces. A plunger engages in the barrel having a lug element and is rotatable relative to the stop sleeve between a position wherein the plunger tip is fully seated in the barrel and another position wherein the plunger may be activated axially to draw a predetermined dosage of liquid contents into the barrel.

10 Claims, 23 Drawing Sheets

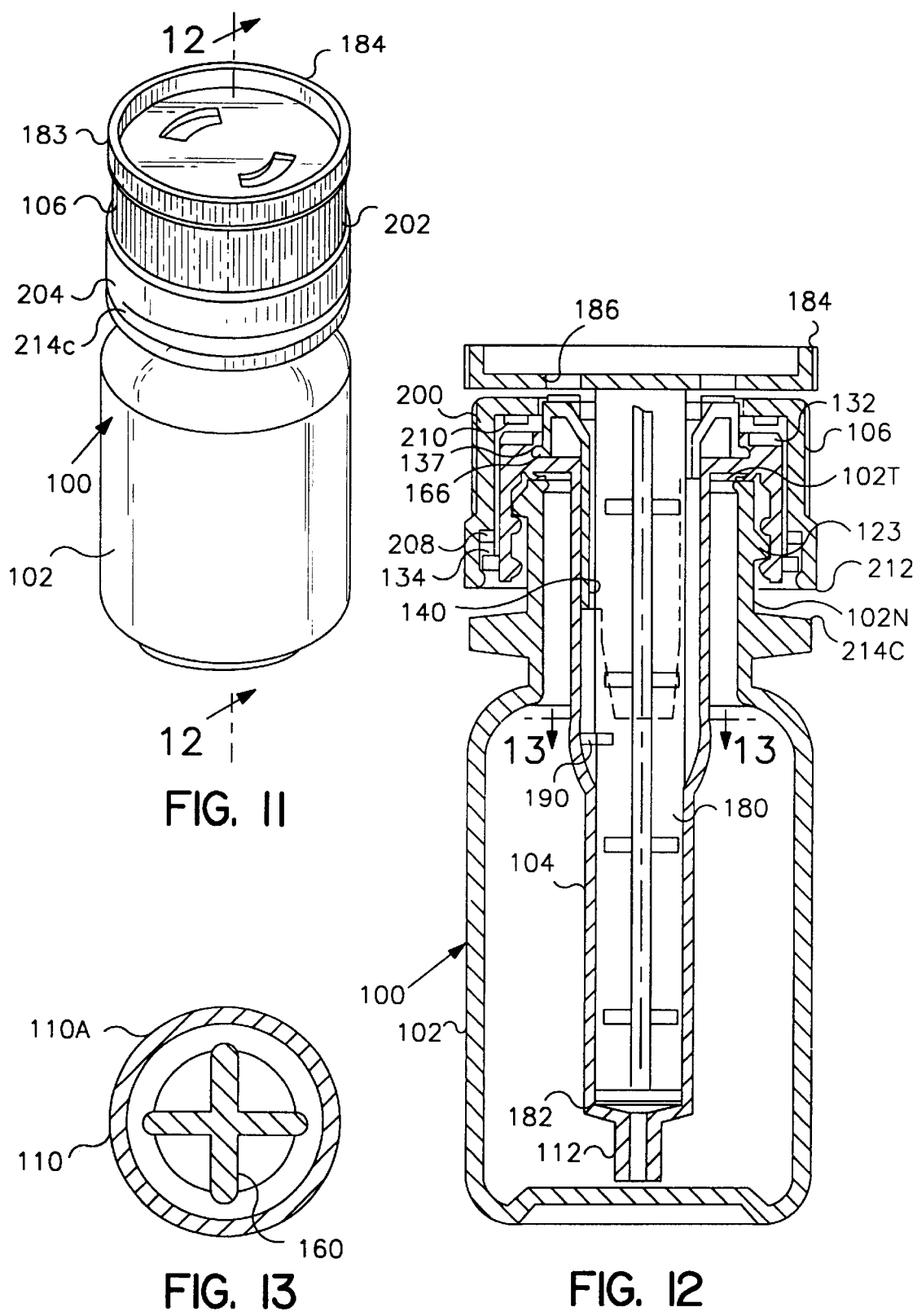

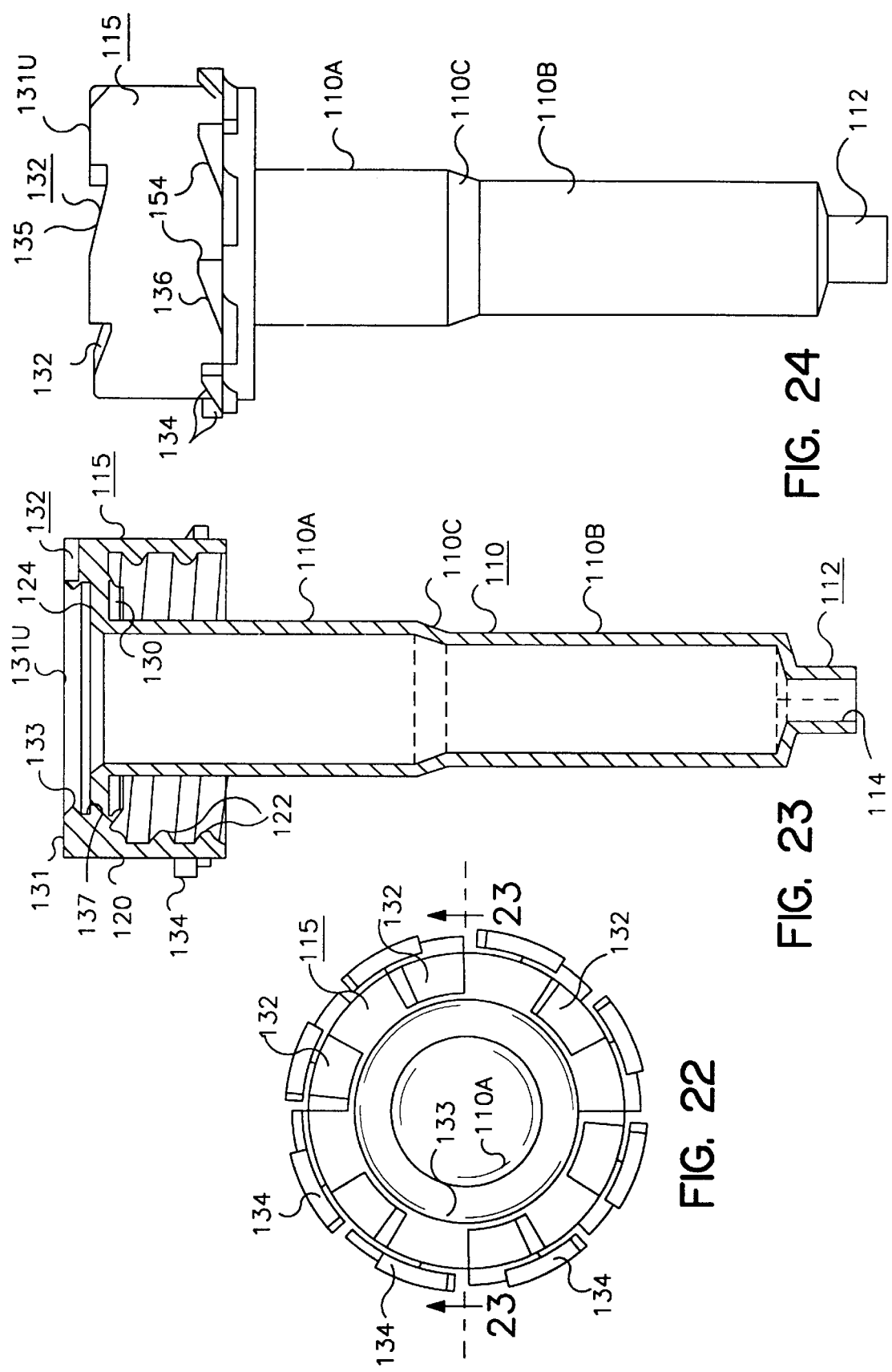

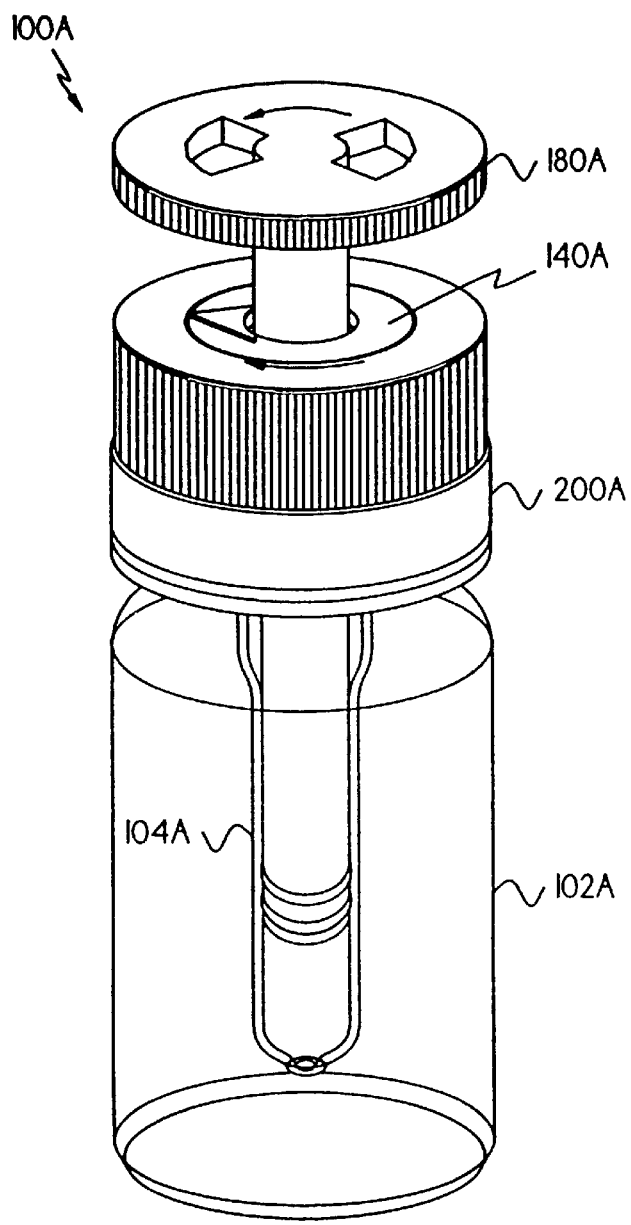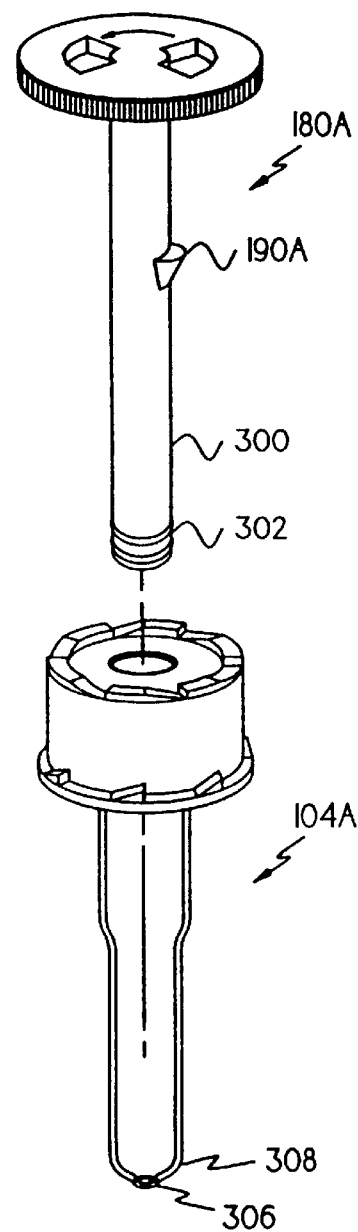
FIG. 30
FIG. 31

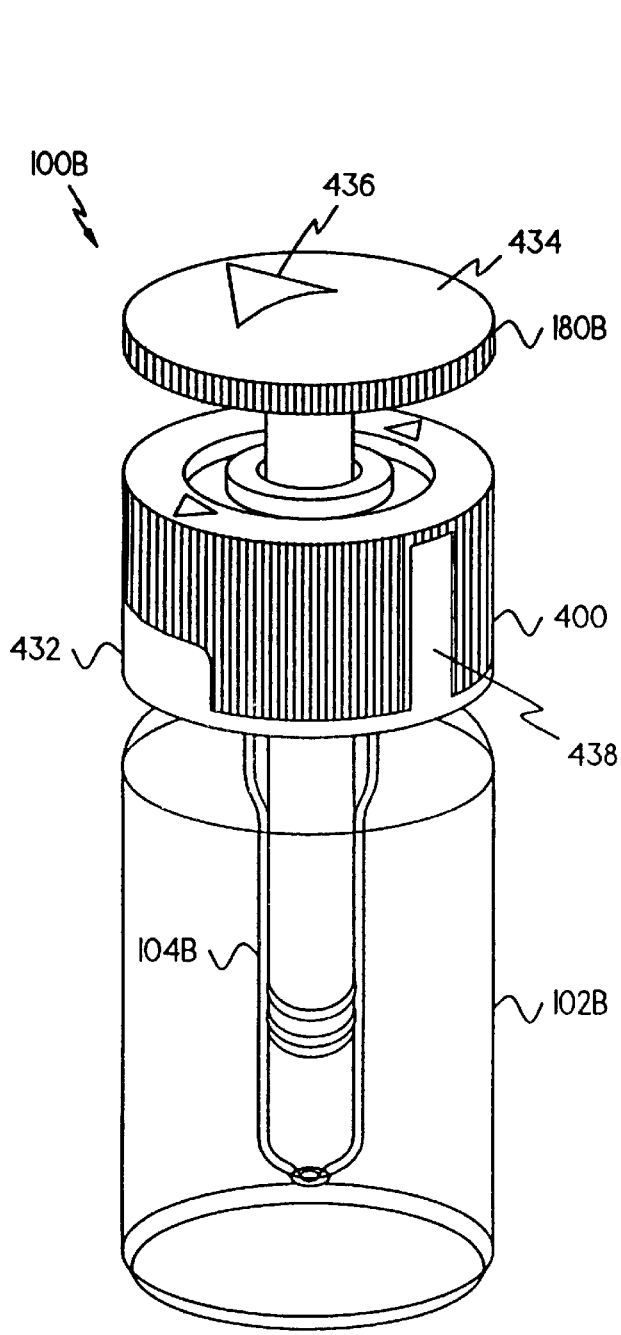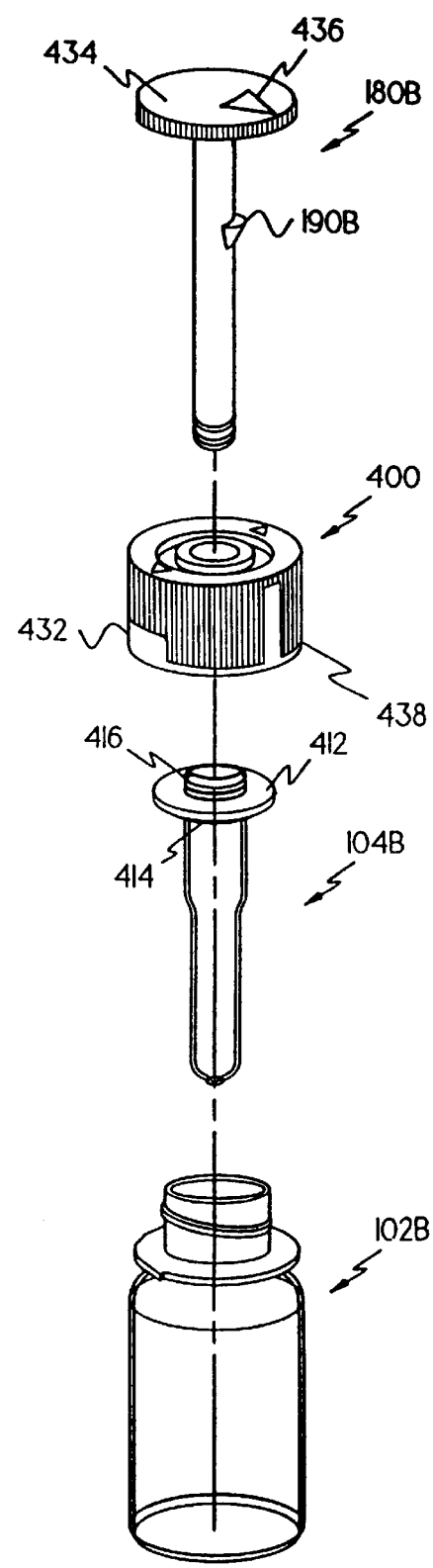
FIG. 35
FIG. 36

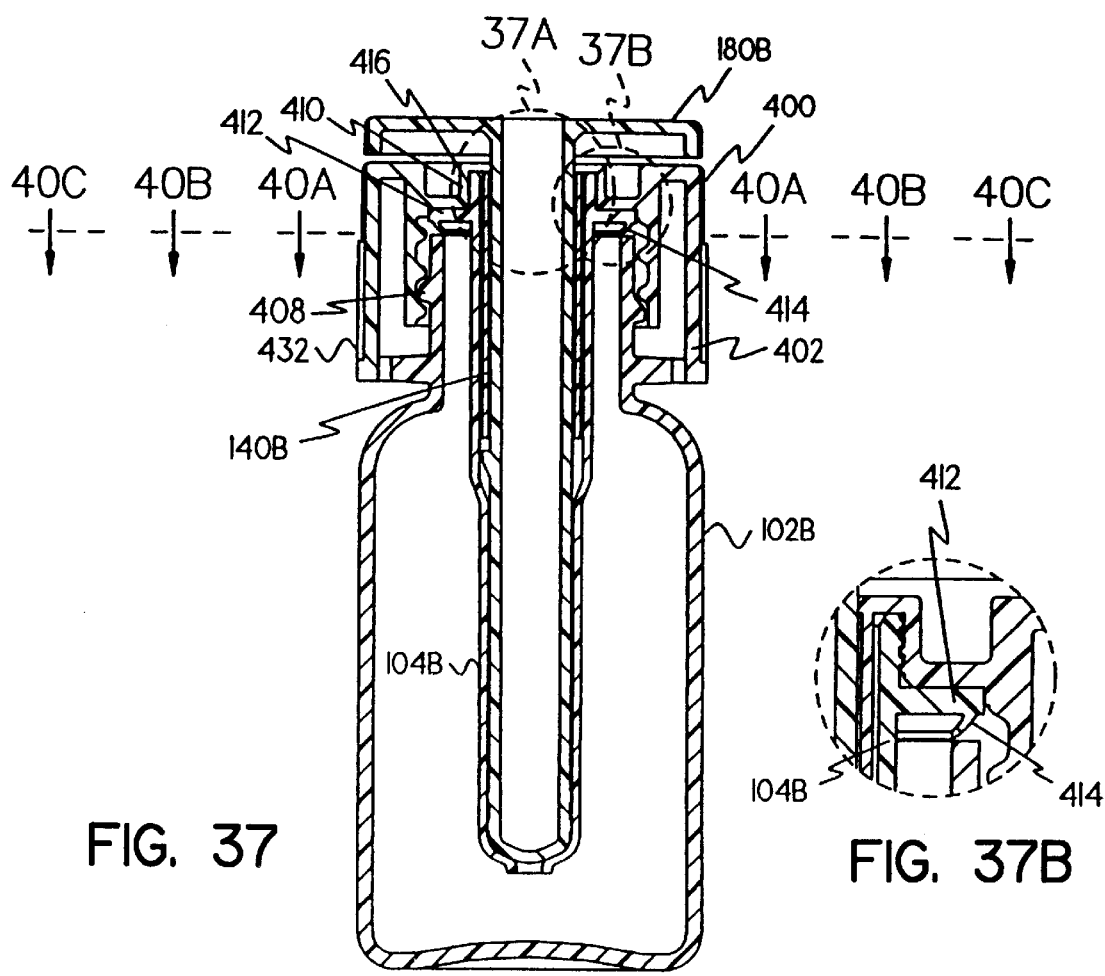
FIG. 37
FIG. 37B
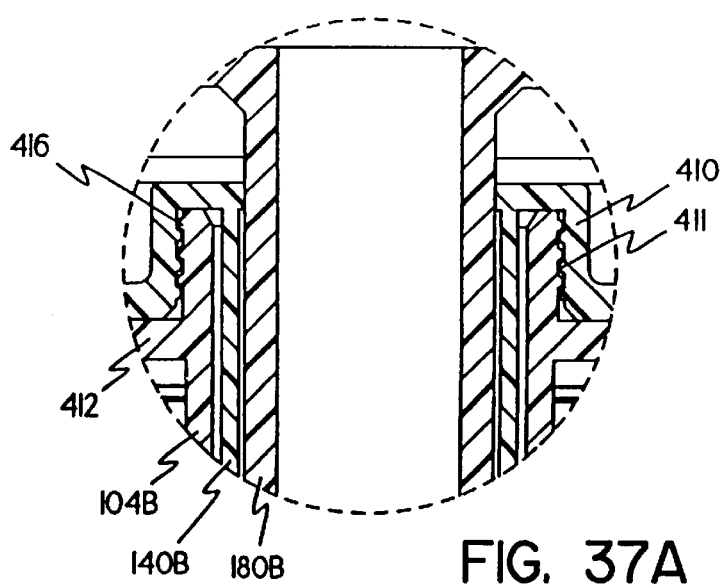
FIG. 37A

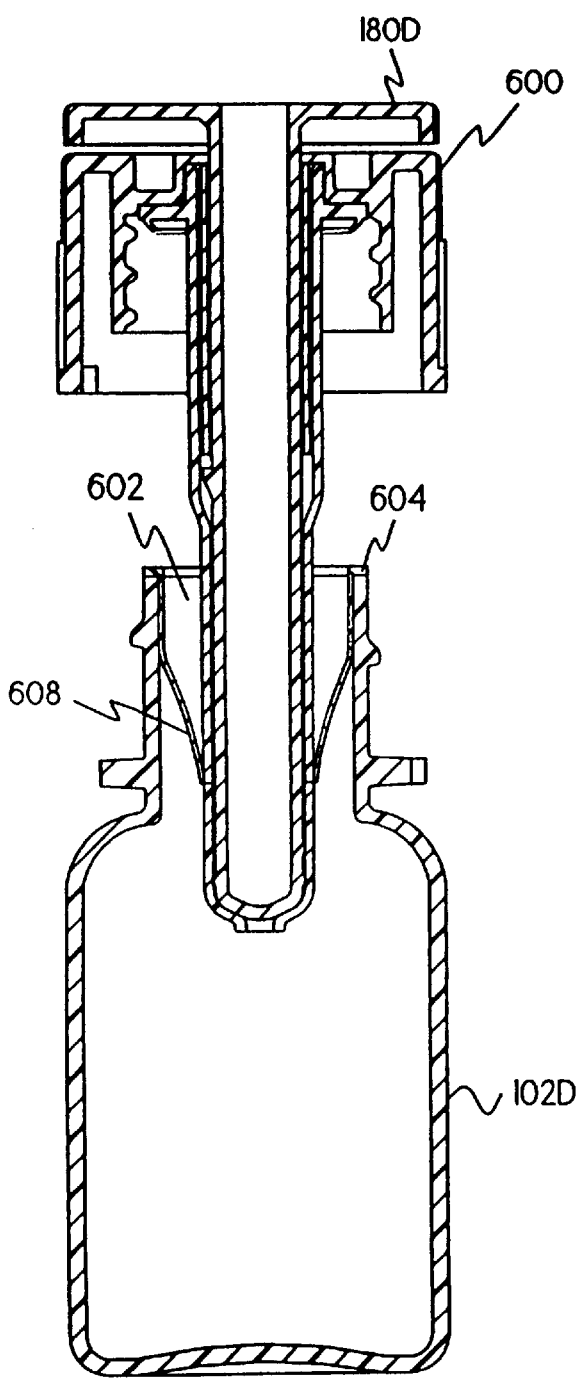
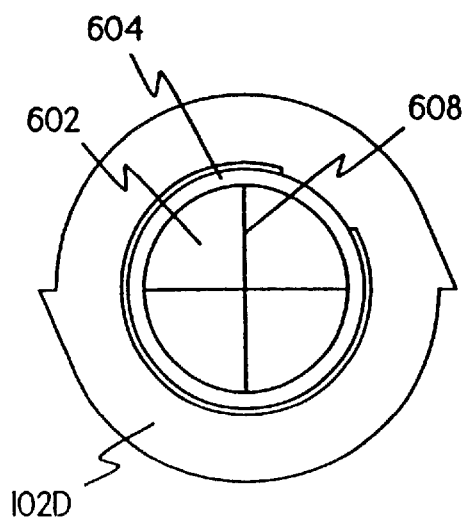
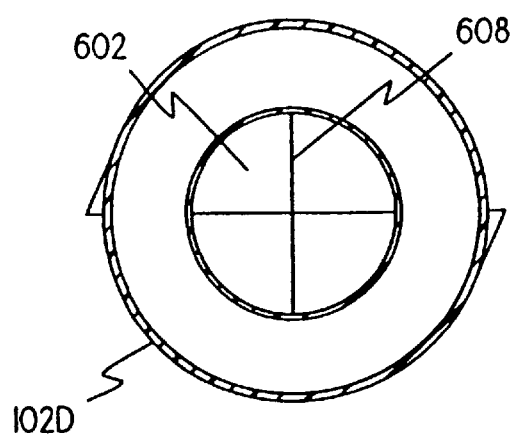
FIG. 46
FIG. 47
FIG. 48

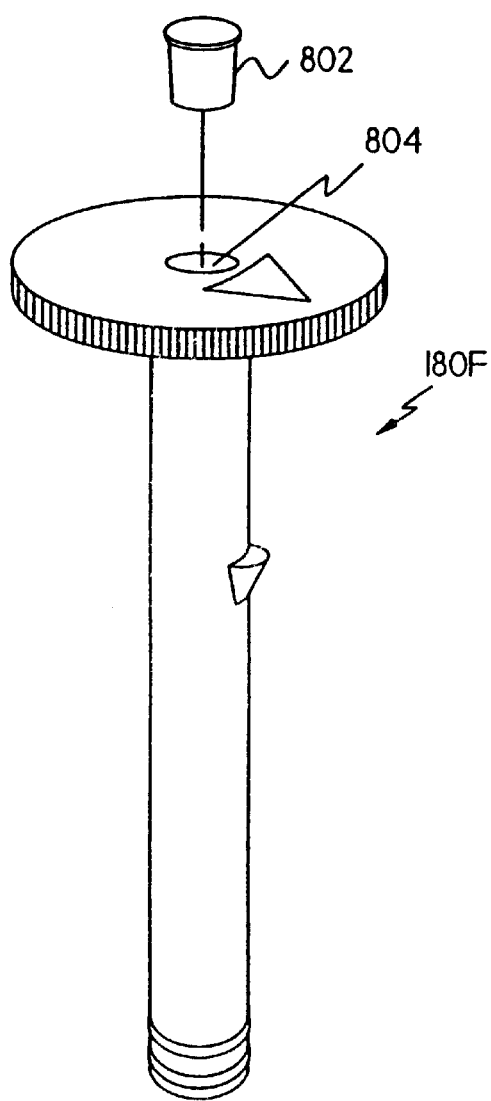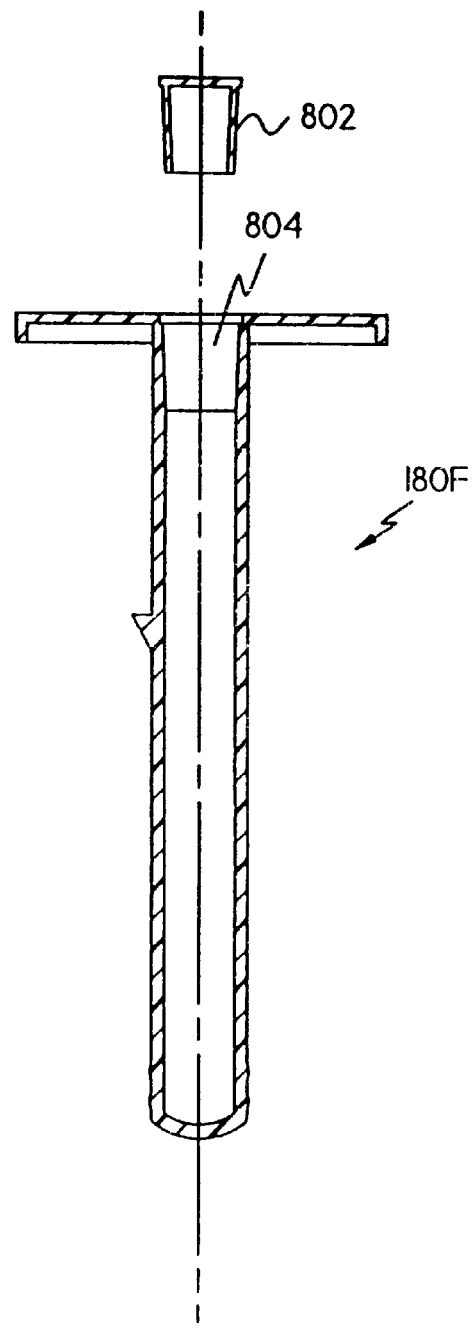
FIG. 50
FIG. 51

EXACT DOSE DISPENSER DEVICE ASSEMBLY

This application claims the benefit of U.S. Provisional Application No. 60/102,436 filed Sep. 30, 1998.

FIELD OF THE INVENTION

While this variable dosage cap has been satisfactory for its intended purpose, it has been characterized by certain disadvantages, particularly in the cost to manufacture the multi-component system, and the necessity of controlling the vacuum created in the bulb for drawings desired dosage into the pipette connected to the bulb.

After considerable research and experimentation, the exact dose dispenser of the present invention has been devised, which is relatively inexpensive to manufacture, is easily adjustable for dispensing an exact desired dosage and includes a child resistant closure.

BACKGROUND OF THE INVENTION

A variable dosage cap-mounted dropper is disclosed in Foyil U.S. Pat. No. 5,154,702, wherein an overcap housing contains a plunger for compressing a conventional closure-mounted bulb a predetermined distance corresponding to various dosages.

In Gargione U.S. Pat. No. 5,316,161, the child resistant closure is connected to the proximate end of the barrel.

SUMMARY OF THE INVENTION

The exact dose dispenser of the present invention comprises, essentially, a syringe barrel having a plurality of axially extending, circumferentially spaced bosses of different lengths integral with the inner surface of the syringe barrel side wall. A plunger is rotatably and slidably mounted in the barrel and is provided with an outwardly extending lug adapted to selectively engage the end of a respective boss when drawing a desired dosage into the syringe barrel. The syringe barrel is provided with a child resistant closure having an inner cap and an outer cap.

The proximate end of the barrel is integral with the inner cap which has dosage indicia carried on the top wall thereof viewable through an aperture in the proximate-end portion of the plunger. The dosage indicia on the top wall of the inner cap is aligned with a respective boss on the inner surface of the syringe barrel, whereby when drawing an exact dose into the syringe barrel, the plunger is pushed inwardly to the retracted position within the syringe barrel. The plunger is then rotated to a selected dosage as indicated by the indicia on the top wall of the inner cap and viewable through the aperture in the proximate-end portion of the plunger. The plunger is then pulled outwardly of the syringe barrel, thereby drawing a volume of medicament into the syringe barrel until the lug on the plunger abuts the end of the respective boss on the inner surface of the syringe barrel. An exact desired dosage is now contained in the syringe barrel which is dispensed therein by pushing the syringe plunger inwardly of the syringe barrel.

BRIEF DESCRIPTION OF THE DRAWINGS

FIG. 11 is an enlarger isometric view showing another embodiment of the metered syringe assembly of this invention;

FIG. 12 is a greatly enlarged sectional elevational view taken on the line 12,12 of FIG. 11 showing the relative positions of all the component parts of the metered syringe shown in FIG. 11 prior to use;

FIG. 13 is an enlarged sectional plan view taken on the line 13,13 of FIG. 12 showing a detail of the interference fit of the stop lug on the dial plunger and the encompassing barrel;

FIG. 22 is an enlarged plan view of the inner cap and barrel assembly;

FIG. 23 is a sectional elevational view taken on the line 23,23 of FIG. 22;

FIG. 24 is a right hand side elevational view of the inner cap and barrel assembly shown in FIG. 23;

FIG. 30 is perspective view of another embodiment of exact dose dispensing assembly in accordance with the present invention;

FIG. 31 is a perspective view of dial plunger and barrel of the assembly shown in FIG. 30.

FIG. 35 is a perspective view of still another embodiment of exact dose dispenser assembly in accordance with the present invention;

FIG. 36 is an exploded perspective view showing the components of the assembly including the dial plunger, closure, barrel and container;

FIG. 37 is a transverse sectional view of the components of the assembly in the assembled position;

FIG. 37a is a detailed view of the of the assembly shown in FIG. 37;

FIGS. 40, 40a, 40b and 40c are transverse sectional views taken on lines 40a—40a, 40b—40b and 40c—40c of FIG. 37 respectively showing the cap or outer shell in a locked position in FIG. 40a and a release position in FIG. 40b and a ratcheting position in FIG. 40c.;

FIG. 46 is a transverse sectional view through the assembly;

FIG. 47 is a transverse view taken generally on lines 47—47 of FIG. 46;

FIG. 48 is a transverse section view taken generally on lines 48—48 of FIG. 46;

FIG. 50 is a perspective view of the dial plunger; and

FIG. 51 is a transverse sectional view of the dial plunger.

DETAILED DESCRIPTION OF THE PREFERRED EMBODIMENTS

Figure 1:
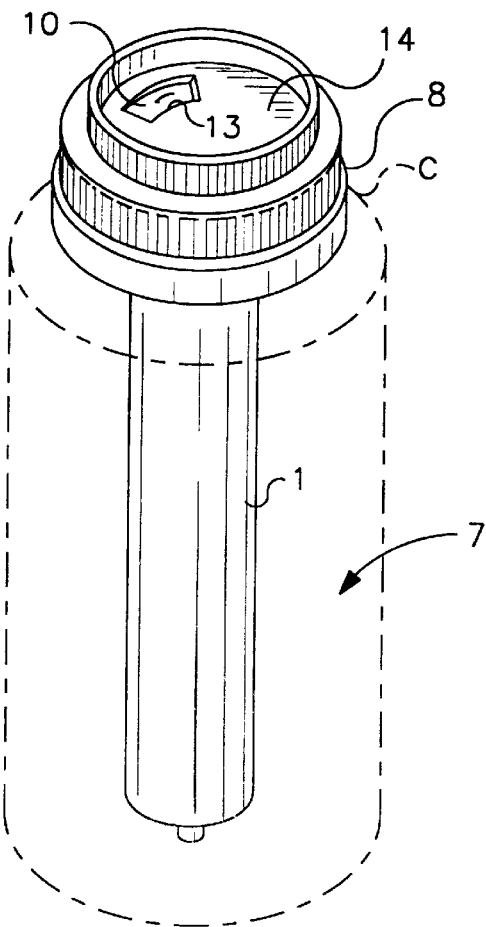
FIG. 1 is a perspective view of a first embodiment of exact dose dispenser assembly in accordance with the present invention.
Figure 2:
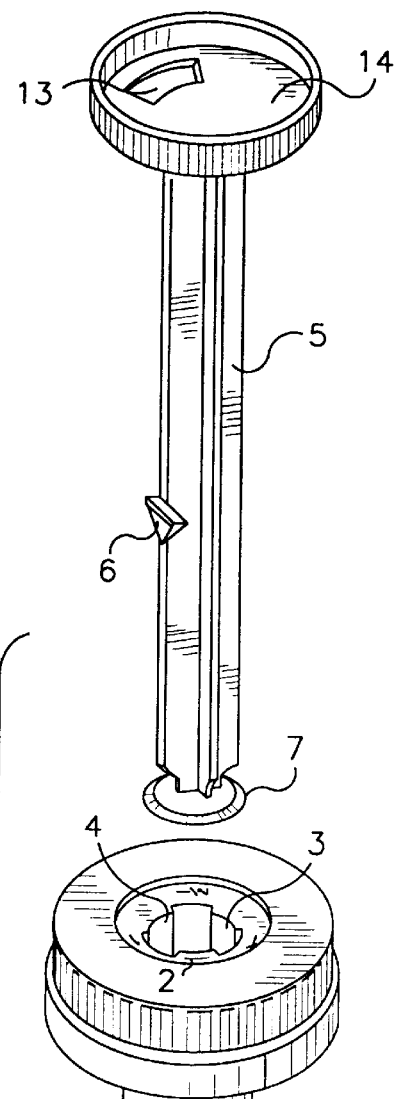
FIG. 2 is a exploded view of a syringe barrel and plunger forming part of the assembly shown in FIG. 1.
Figure 4:
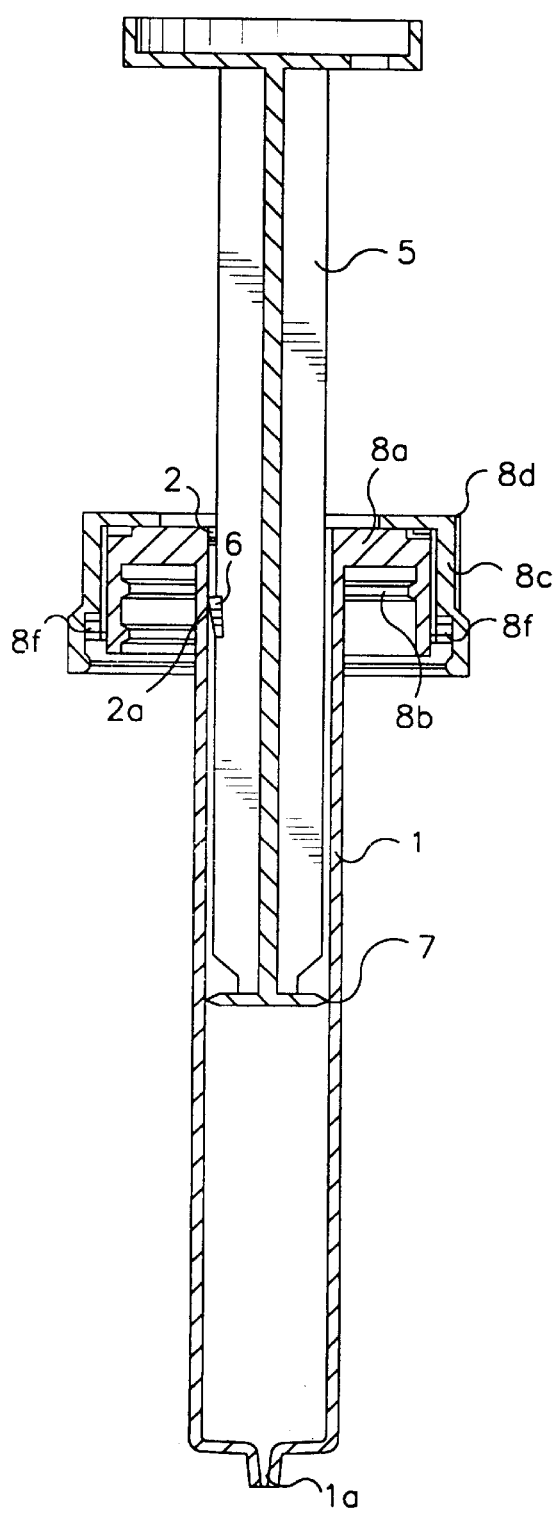
FIG. 4 is an enlarged transverse sectional view showing the parts in position to dispense a first predetermined dosage.

Referring now to the drawings and more particularly FIGS. 1 and 2 thereof, the exact dose dispenser of the present invention comprises a syringe barrel (1) having an outlet ($1^a$) at the distal end there of and a plurality of axially extending, circumferentially-spaced bosses (2), (3) and (4) of different lengths integral with the inner surface of the syringe barrel (1) sidewall. A plunger (5) having a cruciform configuration is rotatably and slidably mounted in the barrel (1) and is provided with an outwardly extending lug (6). The distal end of the plunger (5) is provided with a piston (7) adapted to be in sealing engagement with the inner surface of the syringe barrel (1) sidewall, as shown in FIG. 4. The side wall of the plunger (5) is spaced radially inwardly from the inner surface of the side wall of the barrel and the lug (6) is positioned in this space.

The dispenser of the present invention is provided with a child resistant closure (8) for securing the dispenser to a container (9). The child resistant closure (8) is connected to the proximate end of the barrel (1) and is of the type disclosed in U.S. Pat. No. 5,316,161, owned by the assignee of the instant application, the disclosure of which being incorporated herein by reference. The child resistant closure (8) includes an inner cap ($8^a$) integral with the proximate end of the syringe barrel (1), and having threads ($8^b$) for securing the closure (8) to the neck of the container (9). An outer cap ($8^c$) is rotatably mounted on the inner cap ($8^a$) and is provided with rigid fingers engageable with cooperating rigid teeth ($8^e$) provided on the top surface of the top wall of the inner cap ($8^a$), and additional rigid teeth ($8^f$) cooperating with flexible fingers ($8^g$) on the inner cap.

The inner cap ($8^a$) is normally biased into engagement with the outer cap ($8^c$) for screwing the closure (8) onto the container 9, but the outer cap ($8^c$) and inner cap ($8^a$) become disengaged when the outer cap ($8^c$) is turned in a direction to remove the closure (8) from the container resulting in the outer cap ($8^c$) being freely rotatable on the inner cap ($8^a$). The cooperating teeth ($8^d$), ($8^e$) and ($8^f$) and fingers ($8^g$), provided on the inner and outer caps ($8^a$) and ($8^c$), become engaged when the outer cap ($8^c$) is pushed downwardly to interconnect the inner and outer caps ($8^a$) and ($8^c$) so that the closure (8) and associated dispenser can be removed from the container 9.

Figure 3:
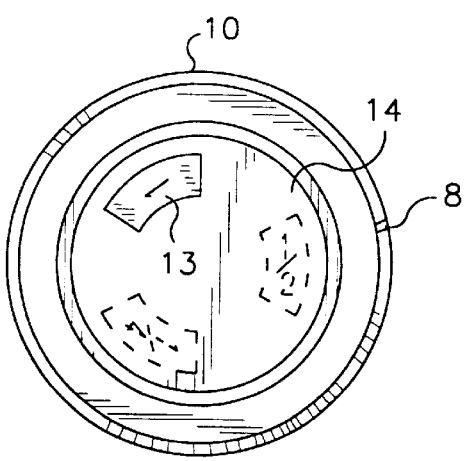
FIG. 3 is a top plan view of the exact dose dispenser assembly of FIG. 1.
Figure 5:
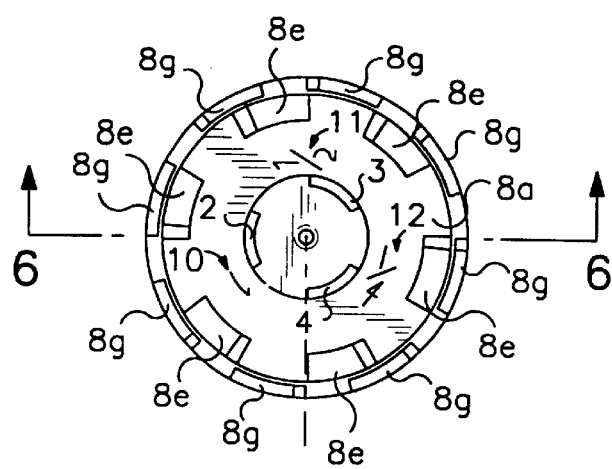
FIG. 5 is a top plan view of the barrel cap portion and an associated inner cap.
Figure 6:
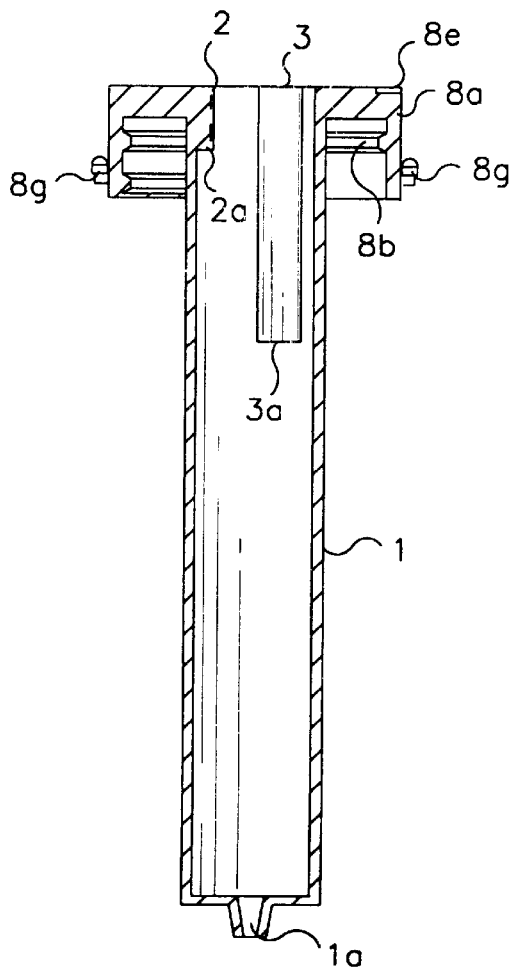
FIG. 6 is a transverse sectional view taken on lines 6,6 of FIG. 5.
Figures 7, 8:
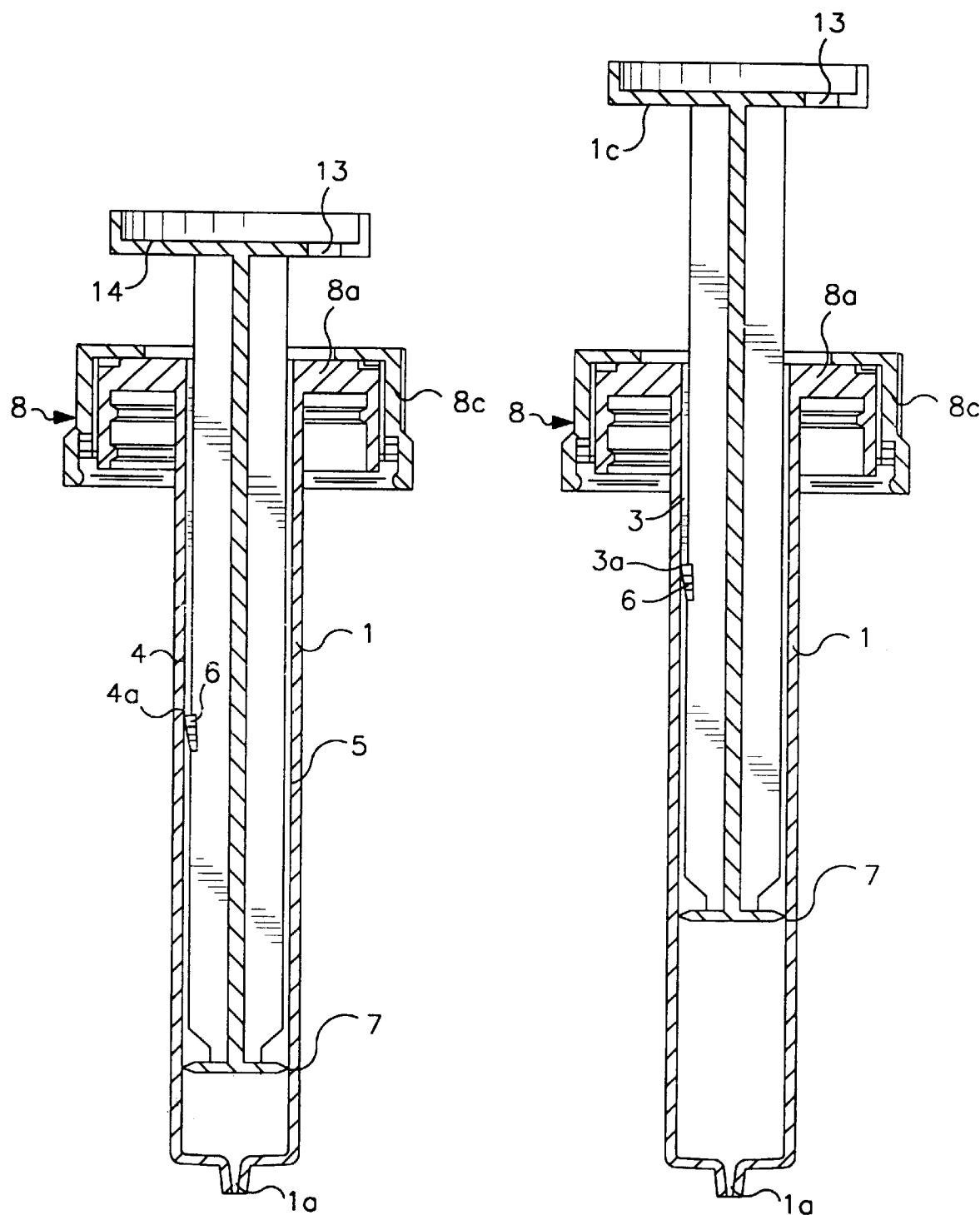
FIGS. 7 and 8 are elongated transverse sectional views through the plunger and barrel showing the position of the parts to dispense second and third predetermined dosages.

As will be seen in FIGS. 1 and 5, the top wall of the inner cap ($8^a$) is provided with dosage indicia (10), (11) and (12), such as "1," ½" and "¼", aligned with a respective boss (2), (3) and (4) on the inner surface of the syringe barrel (1). As will be seen in FIGS. 2 and 3, the indicia (10), (11) and (12) are viewable through an aperture (13) provided in the proximate-end portion (14) of the plunger (5).

In the operation of the exact dose dispenser of the present invention, with the dispenser secured to the container (9), as shown in FIG. 1, and with the plunger (5) pushed inwardly to the fully retracted position within the barrel (1), to dispense a desired dosage, the plunger (5) is rotated relative to the syringe barrel (1) until the desired dosage indicia (10), (11) or (12) appears in the aperture or window (13). The plunger(5) is then pulled outwardly of the barrel (1) to the extended position thereby drawing fluid, such as a medicament, from the container (9) into the barrel (1). The extent to which the plunger (5) can be pulled outwardly, and thus the volume of fluid drawn into the barrel (1) will be limited by the lug (6) abutting the end ($2^a$, $3^a$ or $4^a$) of a selected boss (2), (3) or (4) depending upon the desired dosage. After the desired dosage is contained in the barrel (1), the outer cap ($8^c$) is pushed downwardly to interconnect the inner and outer caps ($8^a$ and $8^c$) so that the closure (8) and the associated dispenser can be removed from the container (9) and the exact dosage dispensed from the syringe barrel (1) by pushing the plunger (5) inwardly to the retracted position within the barrel (1).

From the above description, it will be readily apparent to those skilled in the art that the exact dose dispenser of the present invention is relatively inexpensive to manufacture and is easily adjustable for dispensing exact dosages.

Figure 9:
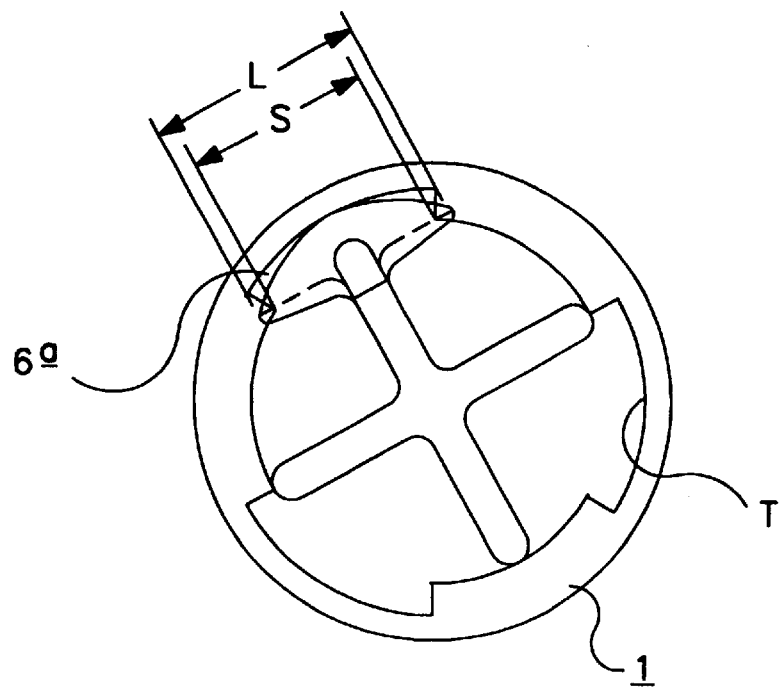
FIG. 9 is an enlarged schematic plan view showing the barrel in plan view in broken line and the plunger section and associated lug in full line having been rotated to an intermediate groove position between the lands of the barrel section showing the width (L) of the lug to be greater than the distance (S) of the land plan preventing withdrawal of the plunger from the syringe barrel after assembly.
Figure 10:
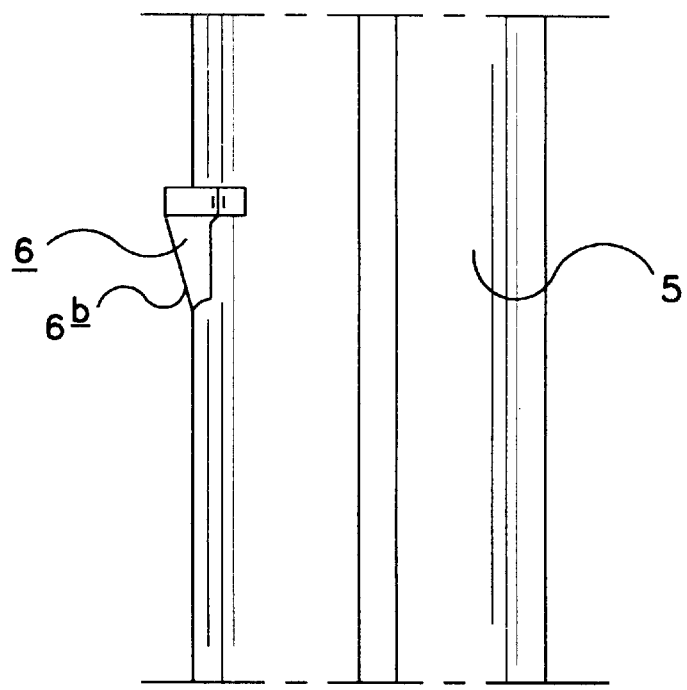
FIG. 10 is an enlarged fragmentary side elevational view of the plunger including the stop lug.
Figure 14:
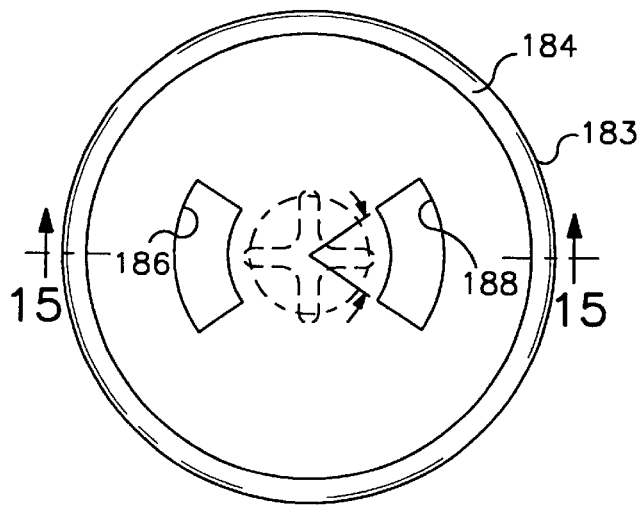
FIG. 14 is a greatly enlarged plan view of the dial plunger assembly.
Figure 16:
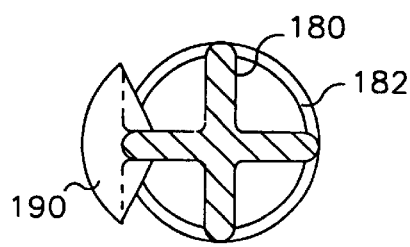
FIG. 16 is an enlarged sectional plan view taken on the line 16,16 of FIG. 15 showing details of the stop lug on the plunger body.
Figure 15:
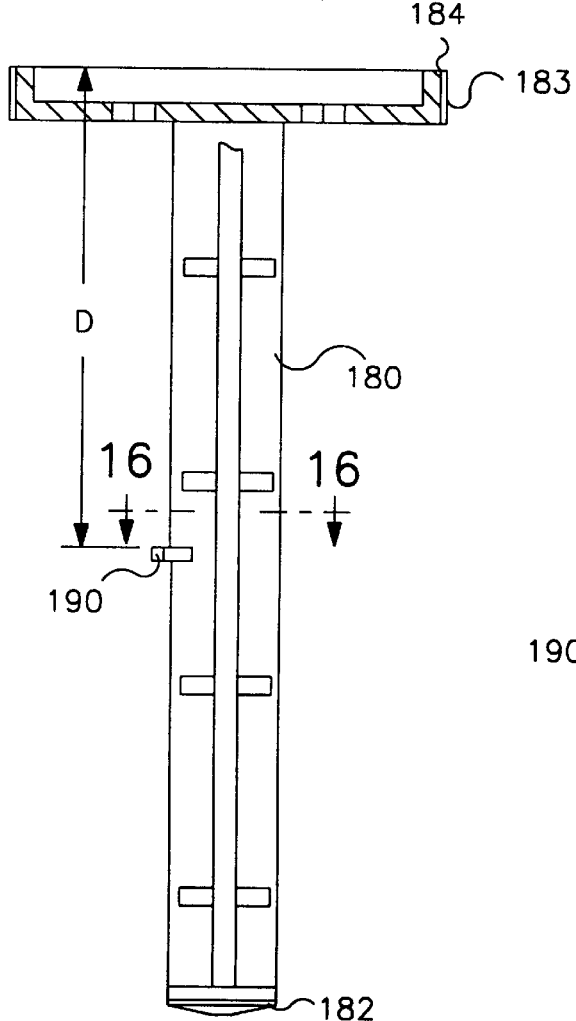
FIG. 15 is a sectional elevational view taken on the line 15,15 of FIG. 14.
Figure 17:
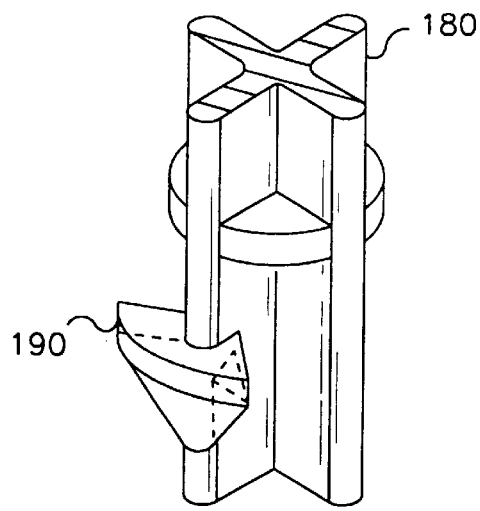
FIG. 17 is an enlarged fragmentary isometric view of a portion of the plunger body including the stop lug.

As shown in FIGS. 9 and 10, the lug (6) is triangularly shaped, the long side (S) having a transverse dimension (L) greater than the width of trackways (T) formed in the barrel (1) so that the plunger is easy to assembly and may not be withdrawn completely from the barrel by reason of the (L) and (S) dimensional relationships. This provides a degree of child resistance or child tamper-proofing for the assembly. Note in FIGS. 9 and 10 that the lug (6) has a gently curved periphery as at (6$^a$) and tapers inwardly slightly as at (6$^b$) for ease of assembly when initially assembling the plunger in the barrel of the syringe assembly.

There is shown in FIGS. 11–29B, inclusive another embodiment of exact dose dispenser assembly in accordance with the present invention generally designated by the numeral 100. The exact dose dispenser assembly includes an elongated hollow plastic container (102) for a product such as a medicament and a syringe sub-assembly (104) mounted in the container (102) via a retainer cap assembly (106).

Considering now, more specifically, the components of the dispenser assembly, consider first the syringe assembly (104). As best illustrated in FIGS. 22–24, the syringe assembly (104) comprises an elongated generally cylindrical hollow barrel (110) terminating at its outer end in a boss or hub (112) having a discharge opening (114) for supporting a syringe needle at the discharge end. A cap portion (115) is integrally formed with the syringe barrel (110) and serves to detachably mount the barrel of the syringe assembly on the container (102). Thus, the cap portion (115) comprises a generally cylindrical circumferentially extending skirt (120) having internal spiral threads (122) which mate with external threads (123) formed on the neck (102N) of the container (102). The skirt (120) is connected via a circumferential radially extending connecting wall (124) to the barrel (110). An inwardly converging frusto-conical sealing lip (130) depends from the interior of the radial wall (124). The lip (130) seals against the axial end face (102$^f$) of the container (102) when the syringe assembly (104) is fully seated on the container (102).

A circumferentially raised rim (131) projects upwardly from the outer periphery of the radial top wall (124). A radially inwardly directed circumferentially extending rib (133) projects inwardly from the inner surface of the rib (131) as best illustrated in FIGS. 22 and 24. The upper face (131$^a$) of the rim has a series of scalloped recesses (132) each having a biased cam surface (135) for a purpose to be described hereafter. The lower edge of the skirt portion (120) has a series of circumferentially spaced, radially outwardly directed fingers (134) which likewise have slanted upwardly directed faces (136) which are slanted in a direction opposite the slant of the cam surfaces (132). The fingers (134) are connected in spaced relation to the skirt portion (120) by connecting links (136) so that the fingers (134) have a limited flexing movement in an axial direction.

Figure 18:
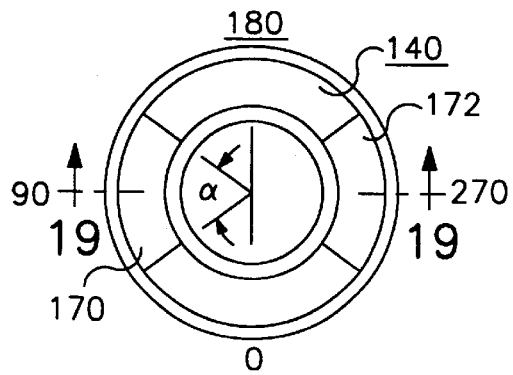
FIG. 18 is an enlarged plan view of the stop sleeve.
Figure 19:
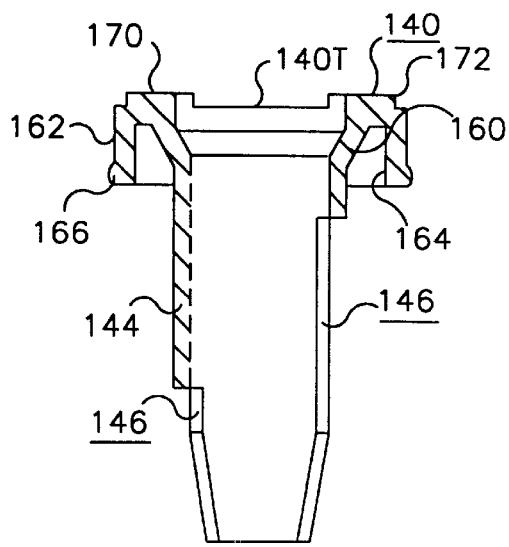
FIG. 19 is a sectional elevational view taken on the line 19,19 of FIG. 18.
Figure 20:
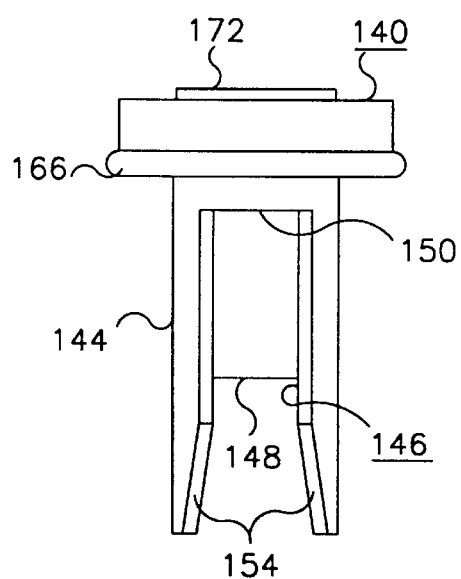
FIG. 20 is a right-hand side elevational view of FIG. 19.
Figure 21:
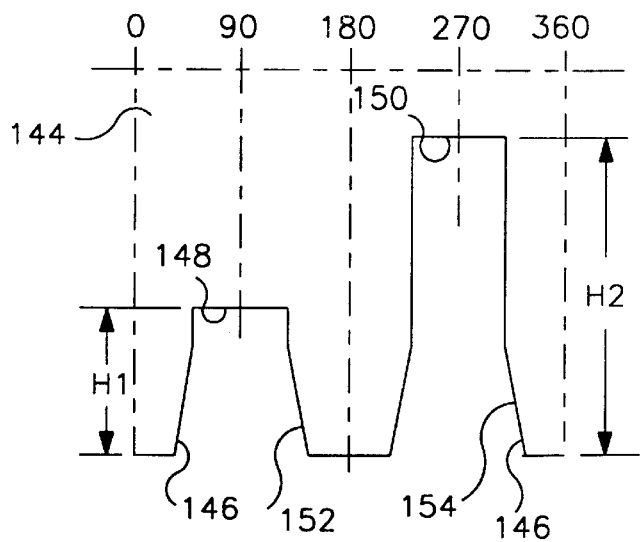
FIG. 21 is a development view of a portion of the stop sleeve barrel.
Figure 25:
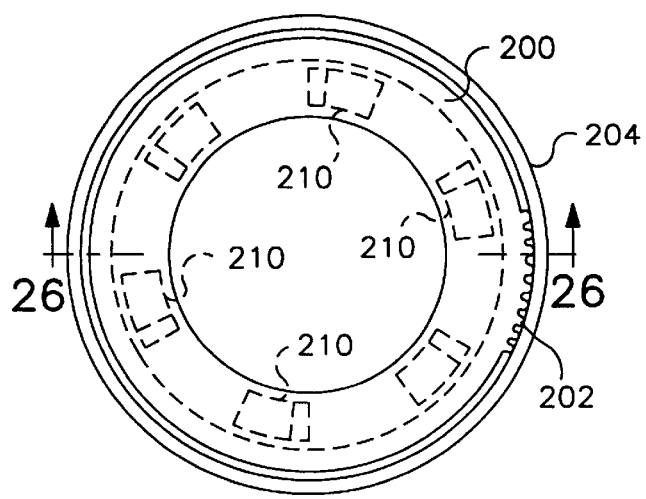
FIG. 25 is an enlarged plan view of the outer shell cap.
Figure 26:
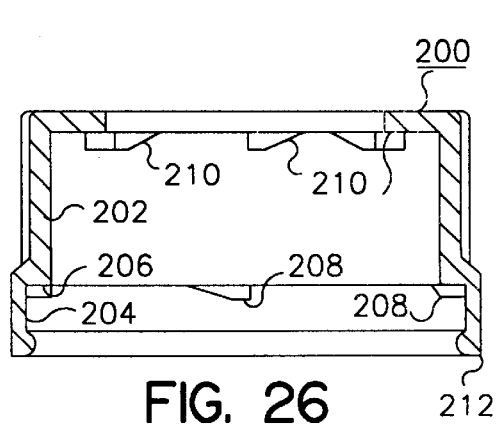
FIG. 26 is a sectional elevational view taken on the line 26,26 of FIG. 25.
Figure 27:
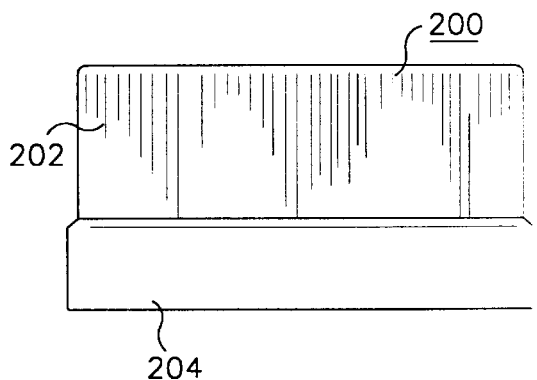
FIG. 27 is a right-hand side elevational view of the outer shell cap shown in FIG. 26.
Figure 28:
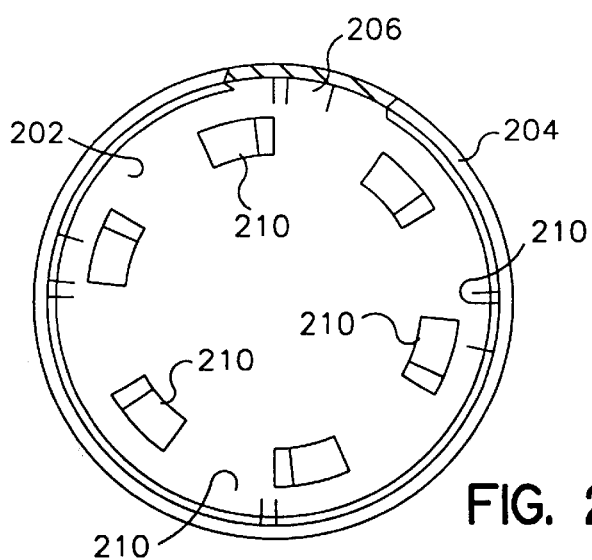
FIG. 28 is a bottom plan view of FIG. 26.

The barrel (110), as best illustrated in FIGS. 23 and 24 is of a stepped configuration defining an upper section (110$^a$) and a lower section (110$^b$) of smaller diameter connected by a frusto-conical section (110$^c$). A stop sleeve (140) nests in the enlarged upper portion (110$^a$) of the barrel. The stop sleeve (140), as best illustrated in FIGS. 18–21, inclusive, comprises an elongated sleeve portion (144) having a series of generally rectangular cut-outs (146) open at the lower terminal end of the sleeve (144) and defining in the present instance, two stops (148) and (150) of different axial heights (H$^1$ and H$^2$), respectively. The side walls of the each cutout (146) are flared outwardly as at (152 and 154), respectively to serve as pilot or guide portions when the plunger lug (6) is in general registry with a selected cutout. The upper end of the sleeve (140) has an upwardly converging frusto-conical wall (160) terminating in a downwardly depending skirt (162) defining a circumferentially depending channel (164) of U-shaped cross-section. The skirt (162) has a radially outwardly directed bead (166) which snap fits past the bead (137) of the barrel cap portion (110) to detachably mount the top sleeve (140) interiorly of the plunger barrel in the manner shown in FIG. 12. When so assembled, the stop sleeve (144) is held in place by the inter-engagement of the beads (166 and 137). The top (140$^r$) of the stop sleeve (140) as best illustrated in FIGS. 18 and 19 has in the present instance two diametrically opposed raised arcuate segments (170 and 172), having an arc α generally equal to the arc (B) of the cutouts (186) and (188) to provide visual indicia for the user and aid in the positioning of the plunger lug (6) in registry with a selected cutout (146) or (148) and in turn providing the means for selectively varying the dosage of product drawn into the syringe in a manner to be described in more detail hereafter.

The exact dose dispenser assembly (100) further includes a syringe plunger (180) having a piston (182) at its outer distal end and an inverted cap (184) at its outer end. The outer periphery of the rim (183) of the cap is serrated to aid the user in rotating the same. The top of the cap (184) has arcuate slots (186) and (188) which are diametrically opposed and of a size and shape to generally conforming to the size and shape of the indicia pads (170) and (172) on the stop sleeve (140). The plunger (180) has a radially projecting lug (190) located between its outer terminal ends and disposed a distance (D) from the top so that it lies below the lower terminal edge of the stop sleeve (140) when the plunger (180) is in a fully seated position as shown in FIG. 12.

Figures 29A, 29B:
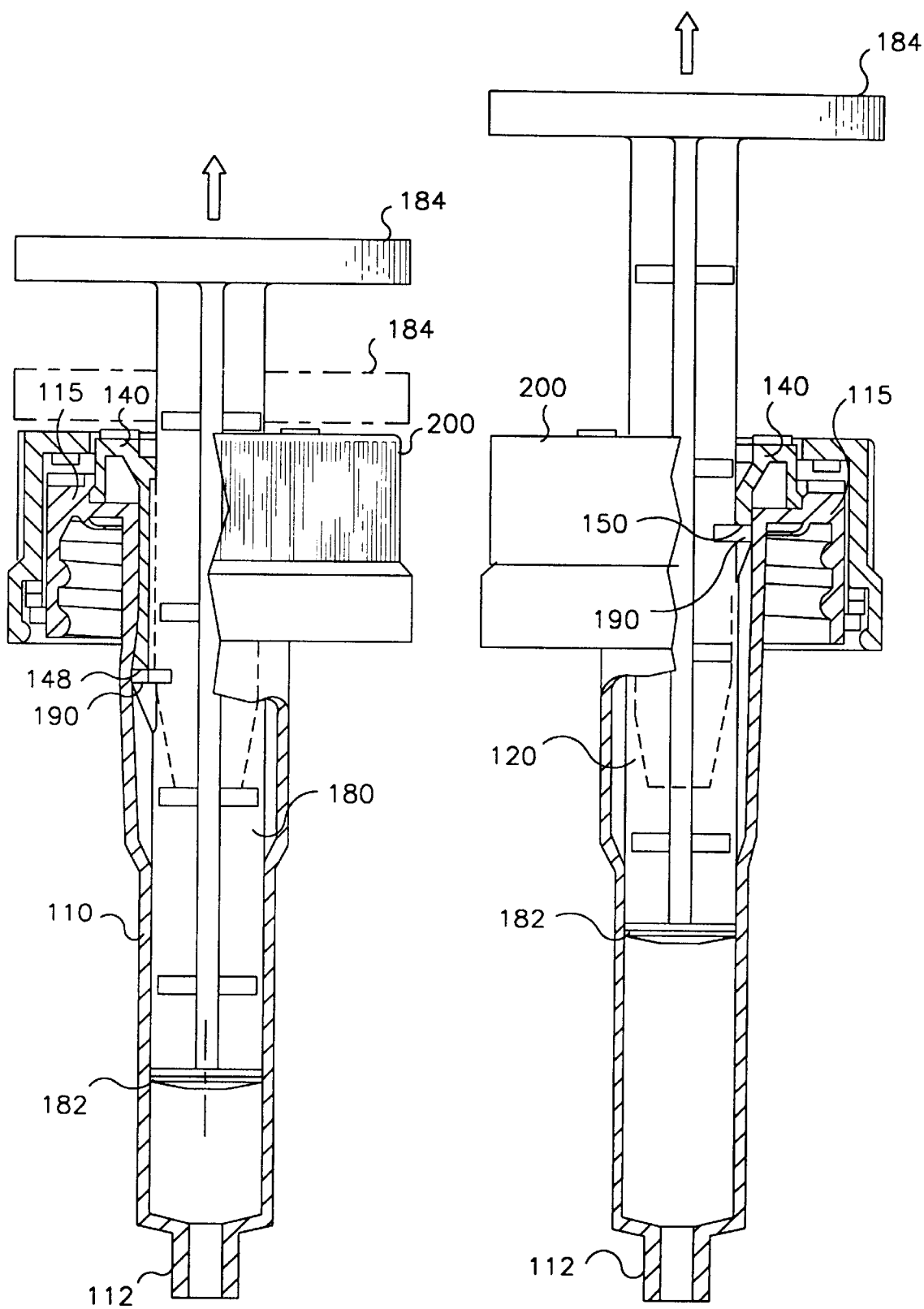
FIG. 29A is a side elevational view similar to FIG. 12 but showing the metered syringe assembly removed from the medicament container having been actuated to entrain 0.4 mL of medicament.
FIG. 29B is a side elevational view similar to FIG. 29A but showing the assembly having been actuated to entrain 0.8 ml of medicament.
Figure 33:
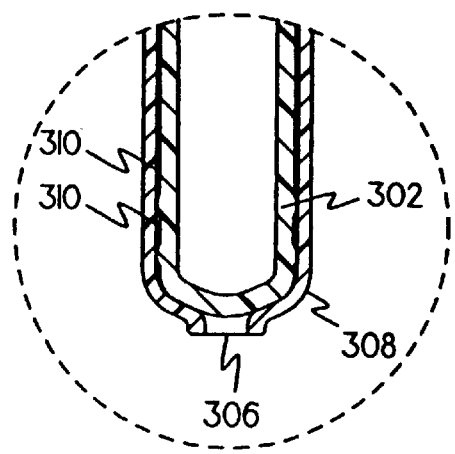
FIG. 33 is an enlarged view of the tunnel end of the barrel and plunger shown in broken lines in FIG. 32.

The exact dose dispenser assembly further includes an outer-shell cap (200) which as best shown in FIGS. 25–28, inclusively, is generally of cup-like form having an upper skirt portion (202) and a lower skirt portion (204) which is stepped outwardly to define a circumferentially extending, downwardly depending face (206) which has a series of circumferentially spaced inclined cams (208) which as best illustrated in FIGS. 12 and 29A overlie and are aligned with rim of the top portion of the barrel. Note that cams (208) are inclined relative to the cam faces (135) so that rotation of the cap (200) in one direction, a counterclockwise direction, simply produces an override, whereas when the cap is rotated in the opposite direction, the axial locking surfaces (210$^a$) and (135$^a$) inter-engage so that the barrel (110) will rotate with the cap (200) in a direction to tighten it on the container. The underside of the top of the outershell cap (200) also has a circumferentially extending equi-spaced series of inclined cams (210) inclined in a direction opposite inclined cams (206), so that when the outershell cap (200) is depressed, the inclined cams (210) can interengage with the scalloped recesses (135) when the outershell cap (200) is rotated in the counterclockwise direction to remove the entire syringe subassembly (104) from the container (102). In addition, the lower terminal edge (212) of the skirt (204) engages the upper face of the container flange (214$^c$) to limit downward movement of the outer shell cap (200) when depressed.

Consider now assembly and use of a exact dose dispenser assembly in accordance with the present invention. The container (102) is first filled with a predetermined quantity of a liquid product. The syringe barrel (110) is then inserted through the open end of the container (102). The barrel (110) is then rotated in a clockwise direction so that the interengaging threads (122 and 123) mesh until the barrel cap portion (116) is fully seated as shown in FIG. 12. Thereafter, the stop sleeve (140) is inserted into the open end of the barrel (110) until it bottoms out and the interengaging rims (137 and 166) are in the position shown in FIG. 12. In this position, the stop sleeve (140) is seated in the barrel (110). The outer shell cap (200) is then positioned over the cap portion (120) of the barrel (110). Note that the spring fingers (134) maintain the actuating cams (208 and 210) on the cap out of engagement with the scalloped slots (132) in the cap portion of the barrel (110). Lastly, the plunger (180) is inserted so that the top (104) overlies the remaining parts in the manner shown in FIG. 12.

Now when it is desired to withdraw a predetermined quantity of product from the container (102), the top (184) of the plunger rod (180) is rotated until the arcuate opening is aligned with the desired quantity to be dispensed, for example, 0.4 ml. The plunger (180) is then actuated axially upwardly. In this position, the lug (6) is aligned with the cutout and the plunger (180) can be displaced upwardly until the lug (190) bottoms on the stop (148). This is the position shown in FIG. 29A. The user then presses the outer cap (200) downwardly against the bias of the spring fingers (134) so that the interior cams of the outer cap (200) engage the cam surfaces (132) on the cap portion of the barrel (110). Rotation of the innercap now in a counter-clockwise direction turns the barrel cap portion in a direction to remove it from the container so that the syringe contents can be withdrawn from the container and cams (208) of the outer cap (200) engage cams (134) of the barrel assembly (110).

Note that the container finish includes a circumferentially extending flange ($214^c$) spaced downwardly from the lower terminal edge of the outer cover at a predetermined distance approximately equal to the displacement distance of the outer cap (200) relative to the internally threaded mounting head of the barrel.

In accordance with the present invention, the desired quantities can be selectively varied from those indicated in the drawings by simply replacing the stop sleeve (140) with a stop sleeve (140) having a different step configuration.

Figure 32:
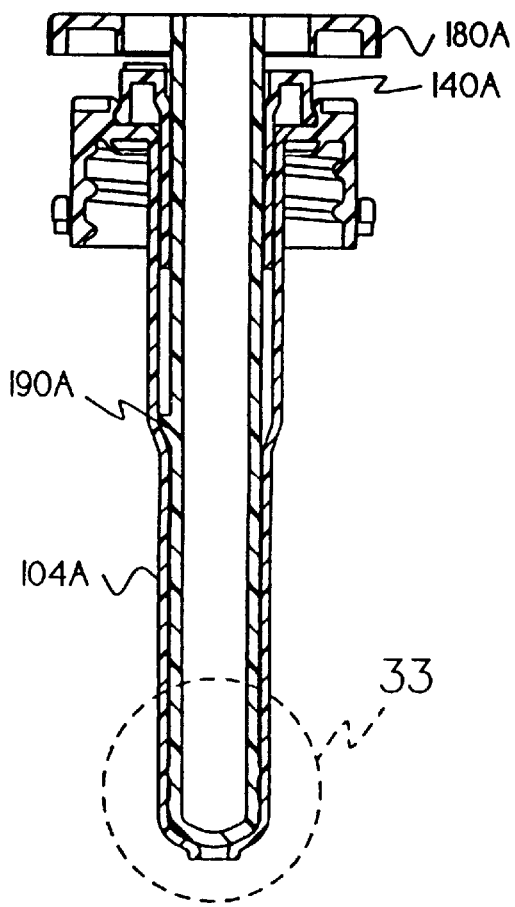
FIG. 32 is a transverse cross-sectional view of the dial and barrel assembly in the nested position.
Figure 34:
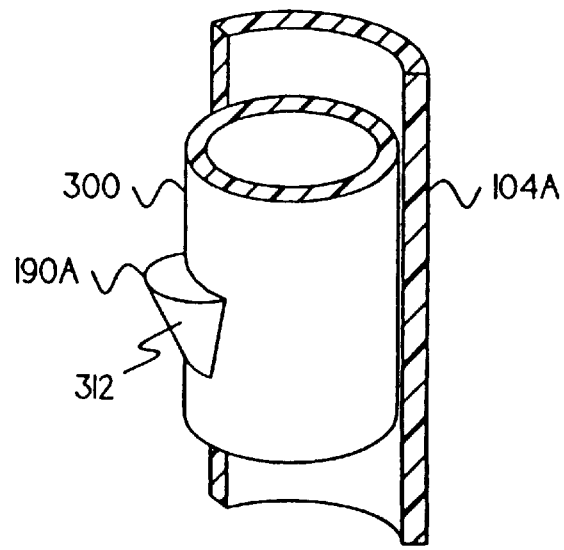
FIG. 34 is a fragmentary perspective view showing the configuration of the cam follower and the plunger.

Referring now to FIGS. 30–34, inclusively, there is shown another embodiment of exact dose dispenser assembly in accordance with the present invention. This embodiment of the invention has components generally similar to the components of the assembly shown in FIGS. 11–29. For ease of understanding therefore, the elements of the assembly shown in FIGS. 30–34, inclusive, are provided with the same reference numeral with an "a" subscript. Accordingly, this embodiment of the invention includes a dial plunger ($180^a$), an outer cap ($200^a$), a stop sleeve ($140^a$), a barrel ($104^a$) The container is designated by the numeral $102^a$. In accordance with this embodiment of the invention, the dial plunger ($180^a$) is an elongated hollow tubular element (300) having a closed arcuate tip portion (302) which conforms generally to the internal configuration of the lower end of the barrel surrounding the discharge opening (306) and designated by the numeral 308. In the present instance, the barrel has a pair of circumferentially extending axially spaced radially outwardly directed sealing ribs (310) spaced upwardly from the lower terminal end of the plunger dimensioned to provide a sealing engagement with the interior wall of the barrel ($104^a$) upon activation of the plunger ($180^a$) axially in the barrel in the manner described previously. The stop lug (190a) has a gently curved outer peripheral surface (312) to conform generally to the offset in the barrel as shown in FIG. 32.

There is shown in FIGS. 35–40b, inclusive, another embodiment of exact dispenser assembly in accordance with the present invention. As in the previously described embodiment, some of the elements of this embodiment are generally similar to those previously described and therefore are given the same reference numeral with, in the present instance, the subscript "b". The assembly which is generally designated by the numeral $100^b$ includes a plunger ($180^b$), a barrel ($104^b$), and container ($102^b$). In the present instance, the outer cap ($200^b$) and the stop sleeve ($140^b$) have been integrated and generally designated by the numeral 4100. In an alternate arrangement a single pad is cooperatively associated with the windows.

As described in more detail hereafter, the various components of this embodiment of the invention are configured in such a way to provide a squeeze and turn operation which, generally speaking, is easier to manipulate.

Considering first the construction of the integrated outer cap-stop sleeve assembly (400), the cap portion ($200^b$) is of generally cup-like form having an outer circumferentially extending skirt portion (402), an inner sleeve member (404) which has internal threads (406) to mate with threads (408) on the neck of the container ($102^b$) to facilitate applying and removing the integrated cap-stop sleeve assembly in the manner described below. The outer cap ($200^b$) has an upstanding central hub portion (410) which is internally ribbed with a series of circumferentially extending ribs (411) to mount the barrel ($104^b$) in the manner shown in FIG. 37. As best illustrated in FIGS. 37 and 37a, the upper end of the barrel ($104^b$) has a radially outwardly projecting collar (412) spaced downwardly from its upper terminal end which has a depending circumferentially extending flexible sealing flange (414) which seats on the axial end of the container adjacent the discharge opening when the parts are in the assembled relationship shown in FIG. 37. The upper wall of the barrel ($104^b$) above the collar 412 has external ribs (416) which engage with the internally ribbed hub (410) of the cap to support the barrel ($104^b$) inside the cap portion ($200^b$) in the manner shown in FIG. 37. The rib arrangement facilitates a press fit and creates a seal between the barrel and outer cap.

Figure 38:
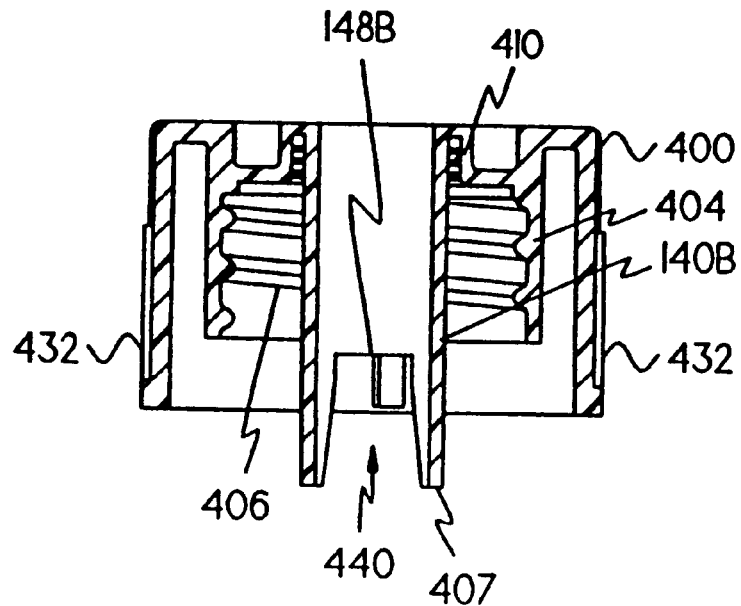
FIG. 38 is a transverse sectional view of the outer cap cam follower element.
Figure 39:
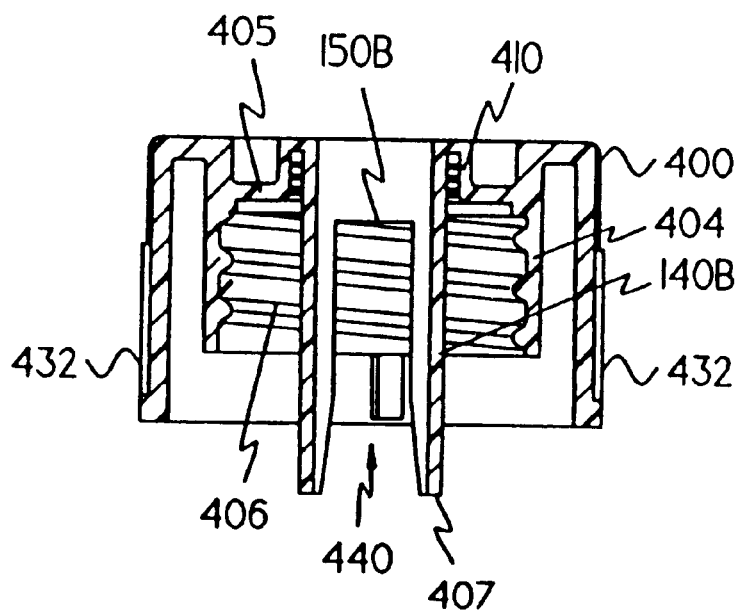
FIG. 39 is a transverse sectional view of the cap cam follower in a 180° position from that shown in FIG. 38.
Figure 40A:
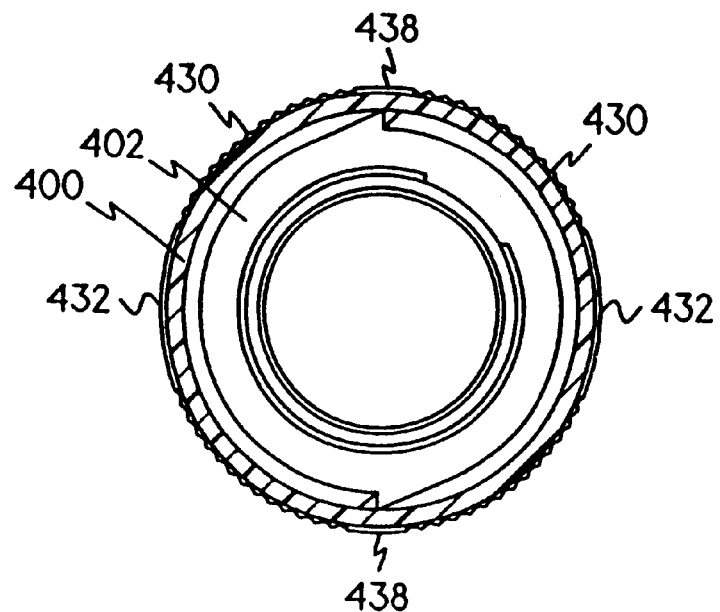
Figure 40B:
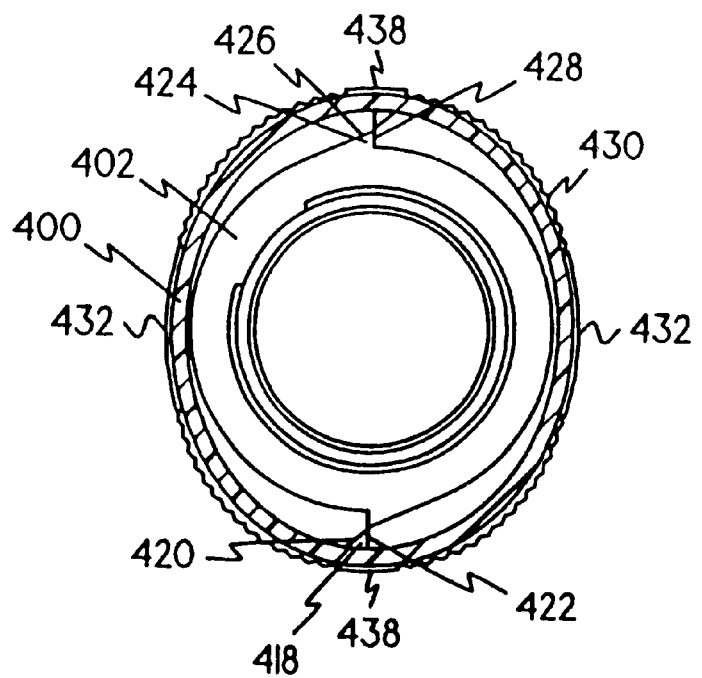
Figure 40C:
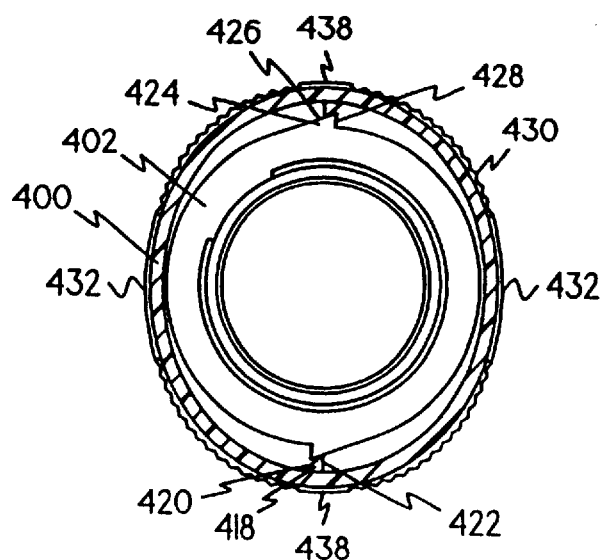
Figure 40D:
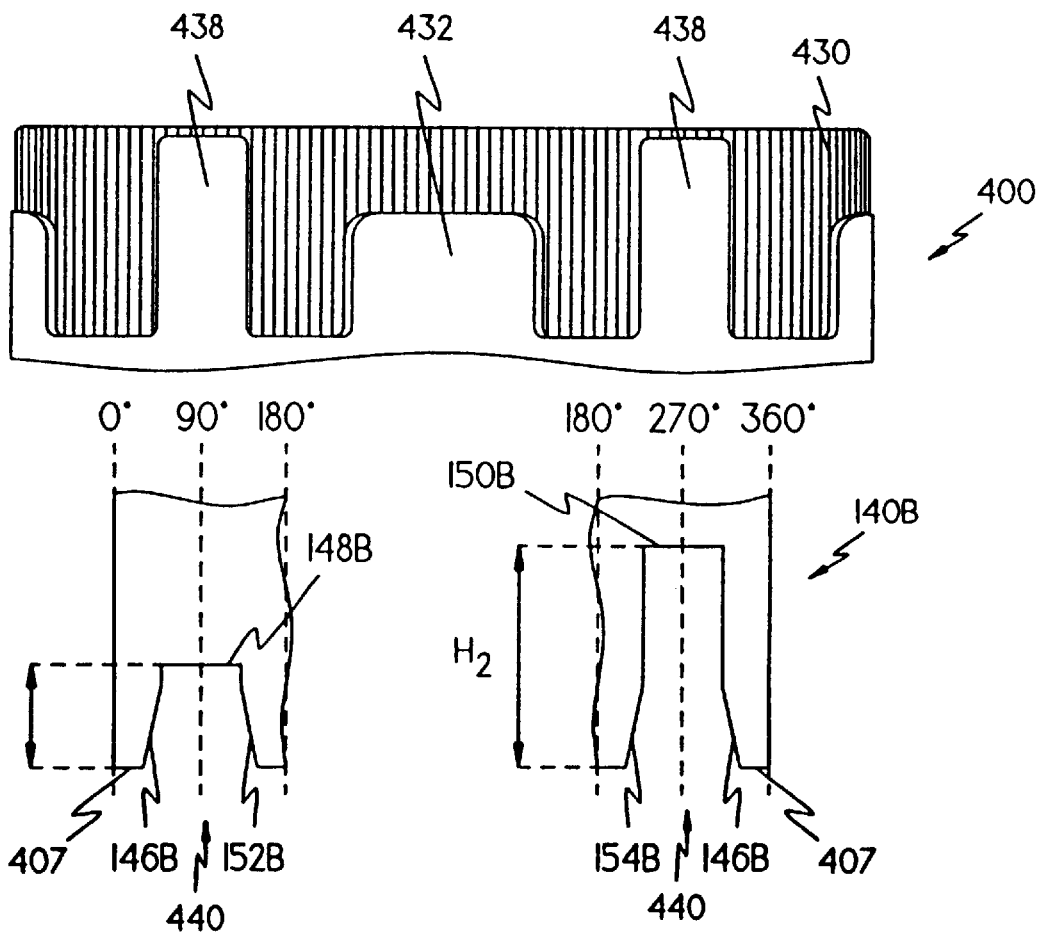
FIG. 40d is a developed view of the closure or cap and the stop sleeve keyways.
Figures 41, 42:
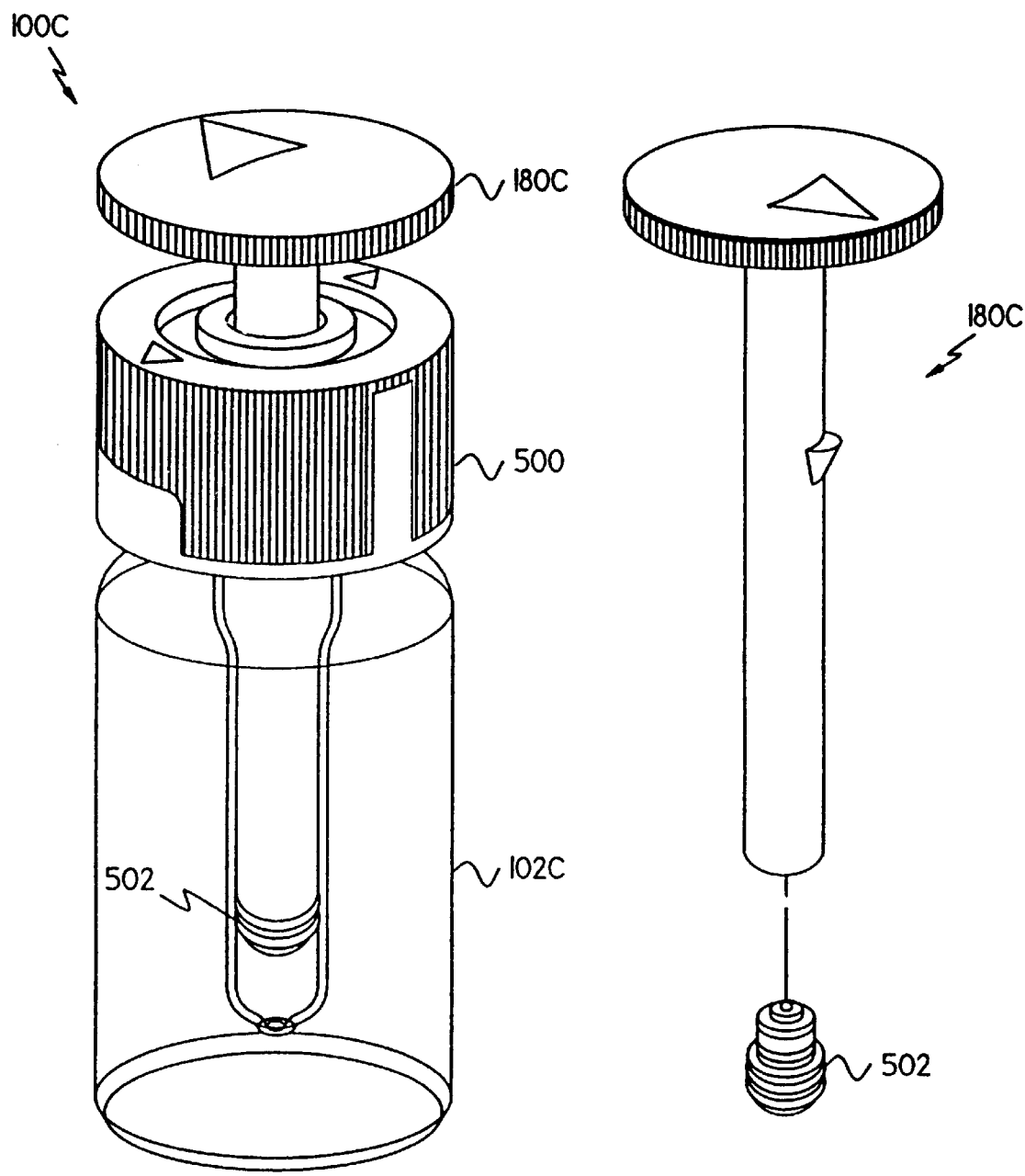
FIG. 41 is a perspective view of still another embodiment of exact dose dispenser assembly in accordance with the present invention.
FIG. 42 is a perspective exploded view of the plunger element.
Figures 43, 44:
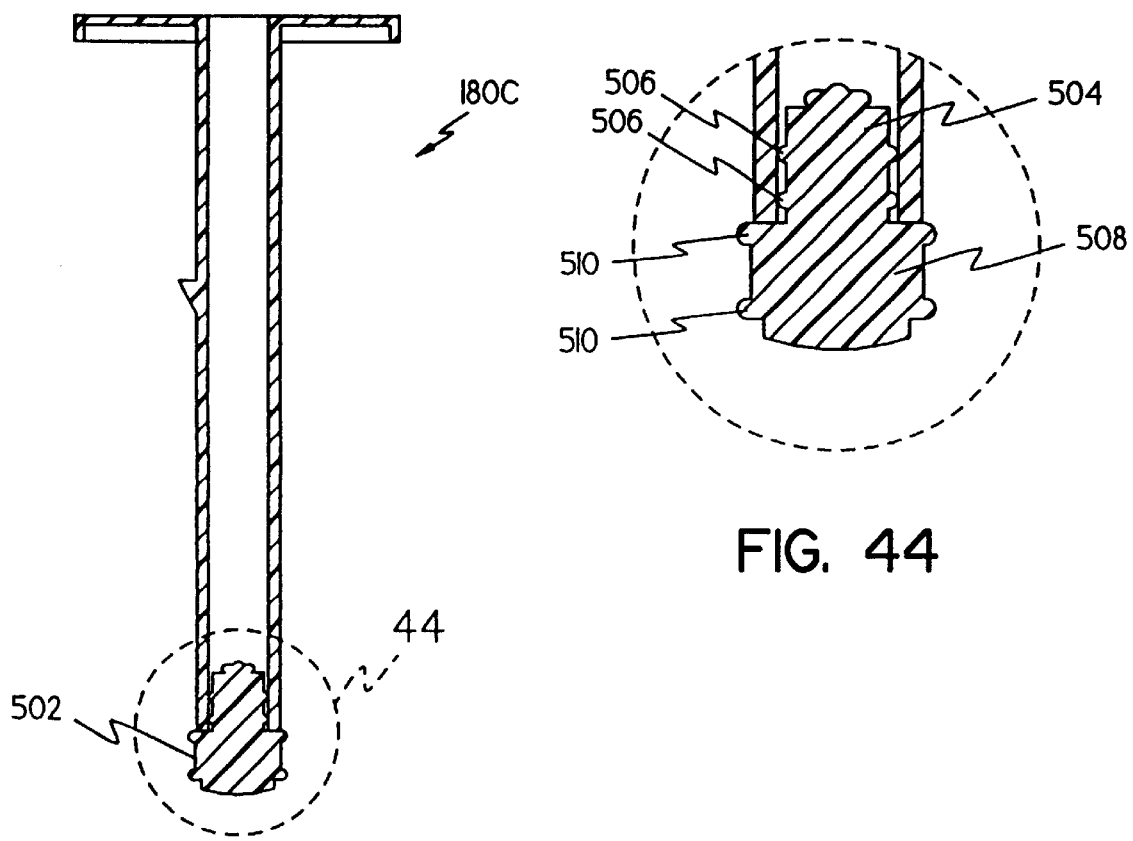
FIG. 43 is a transverse sectional view through the plunger assembly.
FIG. 44 is an enlarged view of the tip end of the plunger portion shown in broken lines in FIG. 43.
Figure 45:
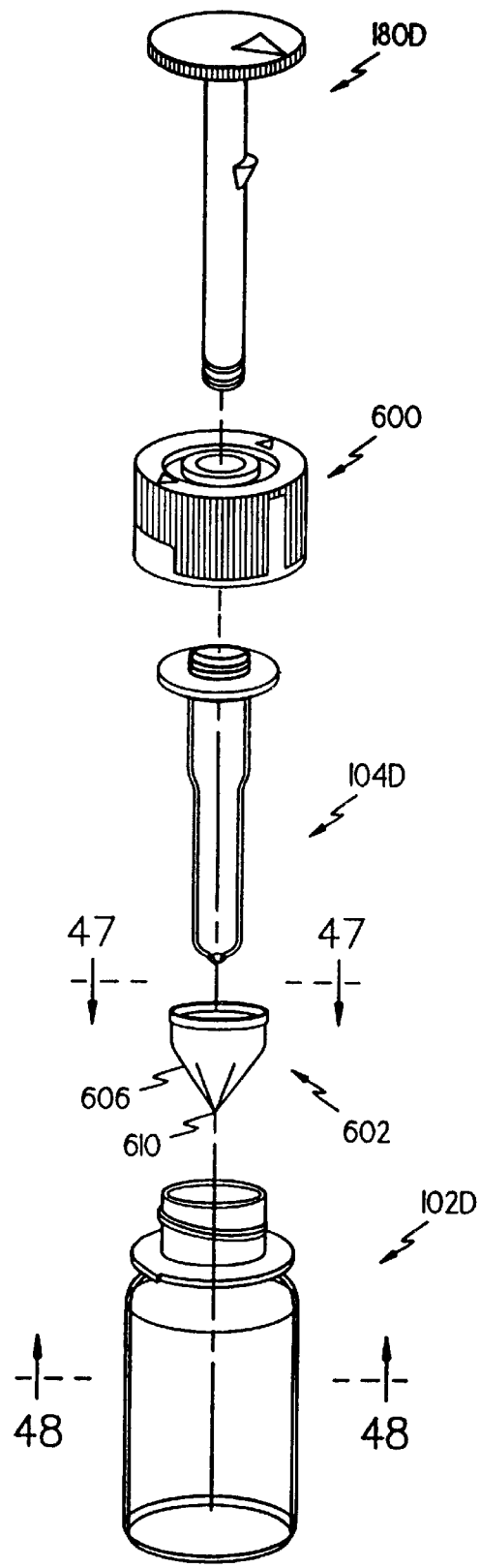
FIG. 45 is an exploded view of still another embodiment of exact dose dispenser assembly in accordance with the present invention.

In the present instance, the stop sleeve is formed integrally with the cap portion ($200^b$) as best shown in FIGS. 37 and 38. Thus the stop sleeve ($140^b$) is formed integrally and is connected to the internally threaded sleeve member (404) a by short radial connecting wall (405). As explained below, the plane P-P through the center of the diametrically opposed keyways ($148^b$ and $150^b$) which define cam surfaces passes through the dose selector portions (438) on the outer periphery of the skirt so that when the user aligns the plunger on either of the dose selectors (438), the cam follower ($190^b$) is aligned with the keyway cam surfaces ($148^b$ and $150^b$) and can be activated by in an axial direction (407). When the cam follower is in intermediate positions, it is aligned with and abuts the lower edge of the stop sleeve (407) to prevent axially upward displacement thereof (see FIG. 29).

The skirt portion (402) of the cap ($200^b$) has a pair of diametrically opposed axially extending lugs (418) which are of a configuration to define a cam surface (420) and a stop surface (422). The disc portion on the container has diametrically opposed complementary lugs or teeth (424) which have a tapered cam surface (426) and a stop surface (428). Accordingly, when the cap ($200^b$) is turned in a clockwise direction to assemble it to the container ($102^b$), the teeth (424) ratchet over the lugs (418) on the container ($102^b$) to permit assembly and when rotated in a reverse direction lock to prevent removal of the cap (200*b*). When it is desired to remove the cap (200*b*), the skirt portion (402) is pressed radially inwardly by the user at diametrically opposed points, as at 432, approximately 90° to the lugs (418) to permit rotation of the cap (200*b*) in a counter-clockwise direction to remove it from the container (102*b*). The serrations (430) on the exterior surface of the skirt portion of the cap is interrupted at the squeeze locations (432) to provide visual indicia to the user. The skirt portion part of the cap is also more flexible in these areas for ease of squeezing and removal of the cap.

The disc-like top (434) of the plunger, has in the present instance, a single indicia in the form of arrow (436) aligned with an arcuate window (438), which in turn is aligned with a channel. The serrations (430) on the skirt portion of the cap is also interrupted at two diametrically opposed locations (438) to provide two dose selectors. Accordingly, when the arrow (436) on the disc-like top of the plunger is aligned with one of the dose selectors (438), the user can now withdraw the plunger. When the user withdraws the plunger, the cam follower (190*b*) is aligned with either the short cam surface (148*b*) in FIG. 38 or the extended cam surface (150*b*) in FIG. 39. The dose selector sections (438) on the outer periphery of the skirt portion 432 are aligned with the cam surfaces (148*b*, 150*b*) in the stop sleeve (140).

There is shown in FIGS. 41–44 inclusive another embodiment of exact dose dispenser assembly in accordance with the present invention, generally similar configuration and operation to the previously described embodiment of FIGS. 35–40*b*. Accordingly, similar part numbers have been given the same reference numeral with the subscript "c".

In this instance, the plunger barrel (180*a*) is an elongated hollow tubular member open at its lower end to receive a plunger piston (502) made of a suitable rubber or plastic material. As illustrated, the piston (502) is of a stepped configuration, having a smaller internal piston portion (504) which engages and seals in the open end of the plunger barrel (104*a*) and has a pair of circumferentially extending ribs (506) providing an interference fit with the internal surface of the plunger barrel (180*c*). The enlarged piston portion (508) likewise has radially outwardly projecting circumferentially extending ribs (510) to engage the interior wall of the barrel (104*a*).

There is shown in FIGS. 45–48 inclusive another embodiment of exact dose dispenser assembly in accordance with the present invention. As in the previously described embodiments like elements such as the barrel (104*d*) container (102*d*) and plunger (180*d*) are given the same reference numeral with the subscript "d". This embodiment is generally similar to the embodiment shown and described in FIGS. 41–43, inclusive, which features the integrated cap and stop sleeve arrangement.

In accordance with this embodiment, generally designated by the numeral (602) a valve (602) which seats in the open end of the container (102*d*) in the manner shown in FIG. 46. The valve (602) is made of a flexible material, such as a polymeric material, and has a flange portion (604) at its upper end and a frusto-conical tip portion (606). The frusto-conical tip portion (606) has a series of slits (608) extending from the pointed tip (610) to allow assembly and removal of the plunger barrel and other components in the manner shown in FIG. 46. The valve (602) functions as a wiper when the barrel and associated elements are withdrawn for a use application to wipe any liquid product on the exterior surface of the barrel.

Figure 49:
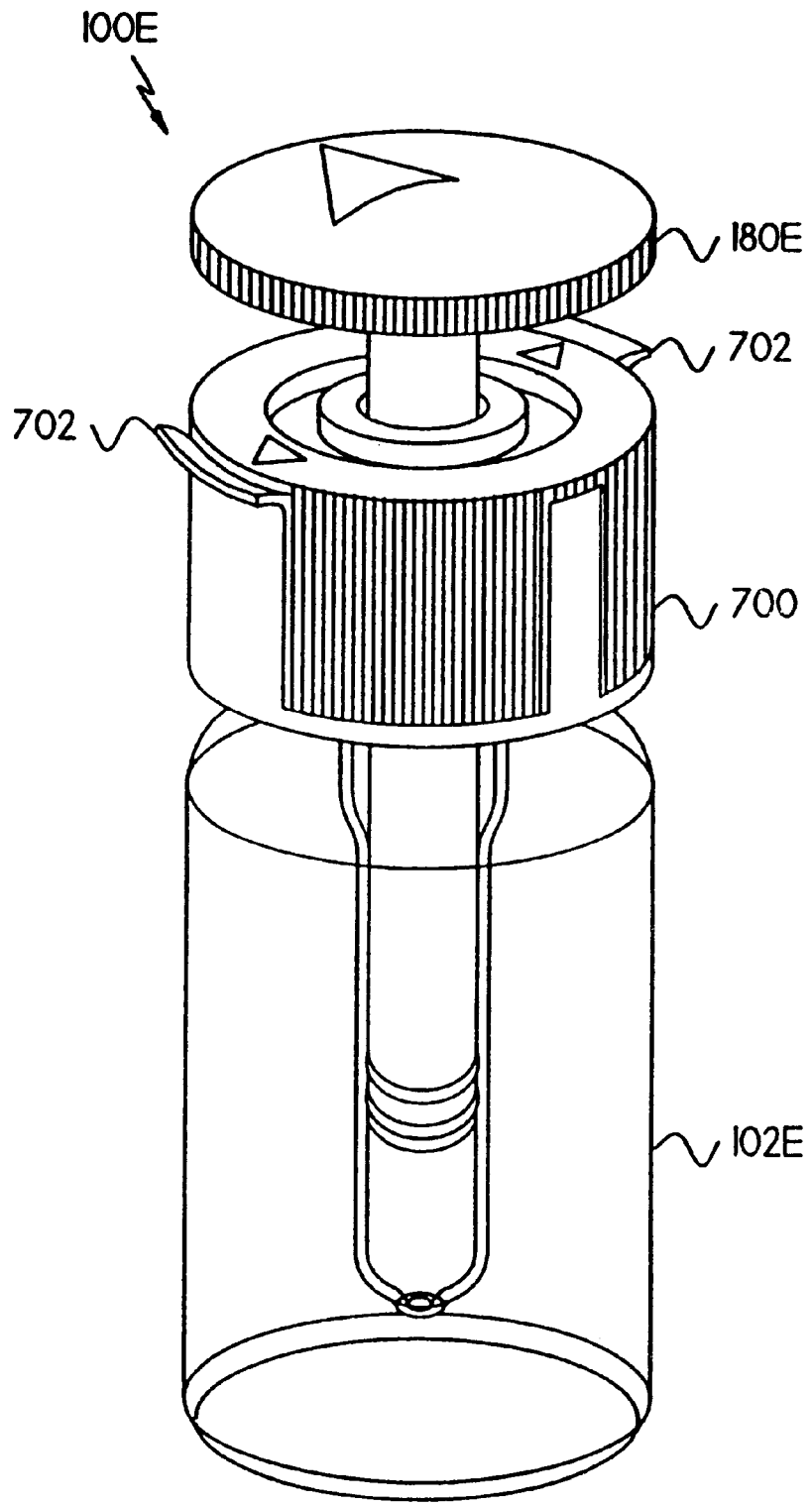
FIG. 49 is a perspective view of a modified embodiment of exact dose dispenser assembly in accordance with the present invention.

There is shown in FIG. 49 another embodiment of exact dose dispenser assembly in accordance with the present invention. This assembly is generally similar to the previously described assembly in terms of components, function and operation. However, in this instance, the skirt portion of the cap is provided with figure grip portions (702) at diametrically opposed locations.

FIGS. 50 and 51 show a modified dial plunger configuration wherein the disc portion has an opening (804) in its upper end aligned to accommodate a plug (802) for an company identification logo or the like.

Even though particular embodiments of the present invention have been illustrated and described herein, it is not intended to limit the invention and changes and modifications may be made therein within the scope of the following claims.

In summary, the secure dose dispenser assembly of the present invention has many features which may be summarized as follows. Secure dose assembly comes as an interval unit, and as part of the package and not as a separate dispenser, that can get disassociated from or lost. The syringe style of the present invention allows complete evacuation of all product in the barrel, regardless of product viscosity, ensuring that the product is dispensed in the proper dosage. The assembly can be easily and economically manufactured, for example, by standard injection molding of plastic materials such as Polyolefin resins. These materials do not present contact or stability issues which rubber or thermoplastic elastomers may present. Other advantages include little or no chance of mis-dosing to a wiper inserted in the container finish to clean the outside of the barrel upon removal as explained in more detail.

What is claimed is:

1. A dosage dispenser assembly for a container having a discharge opening to dispense liquids in the container comprising:

an elongated hollow barrel having a discharge port;

means adapted to removably mount the barrel over the discharge opening in the container so that in the seated position the barrel discharge opening is disposed adjacent the bottom of the container;

a stop sleeve of generally tubular configuration engaging internally of said barrel having at least two key ways of different axial depth defining cam follower surfaces; and a plunger engageable in the barrel having a lug element rotatable relative to the stop sleeve between a position wherein the plunger tip is fully seated in the barrel and another position wherein the plunger may be activated axially to draw a predetermined dosage of liquid into the barrel.

2. A dosage dispenser as claimed in claim 1, wherein said stop sleeve includes a plurality of key ways of different lengths and said lug engages in said key ways when selectively aligned therein.

3. A dosage dispenser as claimed in claim 1, wherein said plunger barrel includes an internally threaded cap portion for positioning and removing the plunger which cooperate with threads on the container finish for selectively assembling and disassembling the plunger barrel from the container.

4. A dosage dispenser as claimed in claim 1, including an outer cap which overlies the cap portion of the plunger barrel and confronting rib means on the outer cap and cap portion of the plunger barrel which are normally spaced apart and which are inter-engageable to permit rotation of the cap portion of the plunger barrel by rotating said outer cap.

5. A dosage dispenser as claimed in claim 1, including biasing means normally positioning the outer cap and cap portion in a position wherein the confronting ribs are spaced apart so that rotation of the outer cap does not effect axial displacement of the cap portion of the plunger barrel.

6. A dosage dispenser as claimed in claim 1, wherein said plunger has a dial with openings for selectively viewing indica means so that the user can selectively position the stop lug on the plunger relative to the keys way in the stop sleeve.

7. A dosage dispenser as claimed in claim 1, wherein the stop sleeve and outer cap are an integral subassembly.

8. A dosage dispenser as claimed in claim 1, including a circumferential extending radially outwardly directed flange on the container finish having a pair of diametrically opposed cam surfaces offset to define locking faces and including a pair of diametrically opposed axially extending ribs on the interior of the skirt which are aligned with and overlie the cam surfaces configured so that in one direction rotation of the outer cap, the lugs override the cam surfaces and rotation in the opposite direction they inter-engaging which the stop surfaces to prevent rotation in a direction to remove the cap portion from the container.

9. A dosage dispenser as claimed in claim 1, wherein the skirt of the cap portion is knurled and is relieved at two diametrically opposed positions approximately 90° removed from the ribs wherein radially inwardly applied pressure at these locations displaces the skirt in the region of the rib portions radially outwardly to permit rotation of the cap portion in a direction to remove it from the container.

10. The combination of a container having a discharge opening and a dosage dispenser assembly, said assembly comprising:

an elongated hollow barrel having a discharge port;

means adapted to removably mount the barrel over the discharge opening in the container so that in the seated position the barrel discharge opening is disposed adjacent the bottom of the container;

a stop sleeve of generally tubular configuration engaging internally of said barrel having at least two key ways of different axial depth defining cam follower surfaces; and a plunger engageable in the barrel having a lug element rotatable relative to the stop sleeve between a position wherein the plunger tip is fully seated in the barrel and another position wherein the plunger may be activated axially to draw a predetermined dosage of liquid into the barrel.

* * * * *